United States Patent
Flaherty

(10) Patent No.: US 7,029,455 B2
(45) Date of Patent: Apr. 18, 2006

(54) DEVICES, SYSTEMS AND METHODS FOR PATIENT INFUSION

(75) Inventor: J. Christopher Flaherty, Topsfield, MA (US)

(73) Assignee: Insulet Corporation, Bedford, MA (US)

(*) Notice: Subject to any disclaimer, the term of this patent is extended or adjusted under 35 U.S.C. 154(b) by 0 days.

(21) Appl. No.: 10/295,806

(22) Filed: Nov. 15, 2002

(65) Prior Publication Data

US 2003/0097092 A1    May 22, 2003

Related U.S. Application Data

(62) Division of application No. 09/943,992, filed on Aug. 31, 2001, now Pat. No. 6,740,059.

(60) Provisional application No. 60/231,476, filed on Sep. 8, 2000.

(51) Int. Cl.
*A61M 37/00* (2006.01)
*A61M 1/00* (2006.01)
*A61M 31/00* (2006.01)

(52) U.S. Cl. ............... 604/131; 604/151; 604/67

(58) Field of Classification Search .......... 700/2; 705/3, 2, 5; 600/365, 573; 604/131–155, 604/890.1, 60–67, 123; 341/176
See application file for complete search history.

(56) References Cited

U.S. PATENT DOCUMENTS

| | | | |
|---|---|---|---|
| 3,631,847 A | 1/1972 | Hobbs | |
| 3,812,843 A | 5/1974 | Wootten et al. | |
| 4,067,000 A | 1/1978 | Carlson | |
| 4,108,177 A | 8/1978 | Pistor | |
| 4,151,845 A | 5/1979 | Clemens | |
| 4,193,397 A | 3/1980 | Tucker et al. | |
| 4,211,998 A | 7/1980 | Junginger et al. | |
| 4,231,019 A | 10/1980 | Junginger et al. | |
| 4,268,150 A | 5/1981 | Chen | |
| 4,342,311 A | 8/1982 | Whitney et al. | |
| 4,364,385 A | 12/1982 | Lossef | |

(Continued)

FOREIGN PATENT DOCUMENTS

DE    4200595    7/1993

(Continued)

OTHER PUBLICATIONS

Web-Site Brochure dated Jan. 4, 2000. MiniMed 508. "Doing its job. Naturally." www.minimed.com/tiles/mm_113.htm.

(Continued)

*Primary Examiner*—Nicholas D. Lucchesi
*Assistant Examiner*—Roz Maiorino

(57) ABSTRACT

A device for delivering a fluid to a patient, including an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. The device also includes a housing free of user input components for providing flow instructions to the local processor, in order to reduce the complexity and costs of the device so that the device lends itself to being disposable in nature. A system and a kit are also described that include the fluid delivery device, a separate, remote control device, and accessories for transcutaneous delivery of fluid medications. Methods of utilizing the fluid delivery device to infuse fluid medications are additionally disclosed.

54 Claims, 12 Drawing Sheets

U.S. PATENT DOCUMENTS

| | | | |
|---|---|---|---|
| 4,373,527 A | 2/1983 | Fischell | |
| 4,424,720 A | 1/1984 | Bucchianeri | |
| 4,435,173 A | 3/1984 | Siposs et al. | |
| 4,469,481 A | 9/1984 | Kobayashi | |
| 4,475,901 A | 10/1984 | Kraegen et al. | |
| 4,498,843 A | 2/1985 | Schneider et al. | |
| 4,507,115 A | 3/1985 | Kambara et al. | |
| 4,514,732 A | 4/1985 | Hayes, Jr. | |
| 4,529,401 A | 7/1985 | Leslie et al. | |
| 4,551,134 A | 11/1985 | Slavik et al. | |
| 4,559,033 A | 12/1985 | Stephen et al. | |
| 4,559,037 A | 12/1985 | Franetzki et al. | |
| 4,560,979 A | 12/1985 | Rosskopk | |
| 4,562,751 A | 1/1986 | Nason et al. | |
| 4,585,439 A | 4/1986 | Michel | |
| 4,601,707 A | 7/1986 | Albisser et al. | |
| 4,624,661 A | 11/1986 | Arimond | |
| 4,634,427 A | 1/1987 | Hannula et al. | |
| 4,678,408 A | 7/1987 | Nason et al. | |
| 4,684,368 A | 8/1987 | Kenyon | |
| 4,685,903 A | 8/1987 | Cable et al. | |
| 4,734,092 A | 3/1988 | Millerd | |
| 4,755,173 A | 7/1988 | Konopka et al. | |
| 4,781,688 A | 11/1988 | Thoma et al. | |
| 4,781,693 A | 11/1988 | Martinez et al. | |
| 4,801,957 A | 1/1989 | Vandemoere | |
| 4,808,161 A | 2/1989 | Kamen | |
| 4,836,752 A | 6/1989 | Burkett | |
| D303,013 S | 8/1989 | Konopka | |
| 4,855,746 A | 8/1989 | Stacy | |
| 4,871,351 A | 10/1989 | Feingold | |
| 4,882,600 A | 11/1989 | Van de Moere | |
| 4,886,499 A | 12/1989 | Cirelli et al. | |
| 4,898,578 A | 2/1990 | Rubalcaba, Jr. | |
| 4,898,579 A | 2/1990 | Groshong et al. | |
| D306,691 S | 3/1990 | Arai | |
| 4,944,659 A | 7/1990 | Labbe et al. | |
| D311,735 S | 10/1990 | Arai et al. | |
| 4,969,874 A | 11/1990 | Michel et al. | |
| 4,973,998 A | 11/1990 | Gates | |
| D315,727 S | 3/1991 | Arai et al. | |
| 5,007,458 A | 4/1991 | Marcus et al. | |
| 5,045,871 A | 9/1991 | Reinholdson | |
| 5,062,841 A | 11/1991 | Siegel | |
| 5,109,850 A | 5/1992 | Blanco et al. | |
| 5,125,415 A | 6/1992 | Bell | |
| 5,176,662 A | 1/1993 | Bartholomew et al. | |
| 5,178,609 A | 1/1993 | Ishikawa | |
| 5,189,609 A | 2/1993 | Tivig et al. | |
| 5,205,819 A | 4/1993 | Ross et al. | |
| 5,213,483 A | 5/1993 | Flaherty et al. | |
| 5,232,439 A | 8/1993 | Campbell et al. | |
| 5,239,326 A | 8/1993 | Takai | |
| 5,242,406 A | 9/1993 | Gross et al. | |
| 5,244,463 A | 9/1993 | Cordner, Jr. et al. | |
| 5,254,096 A | 10/1993 | Rondelet et al. | |
| 5,257,980 A | 11/1993 | Van Antwerp et al. | |
| 5,281,202 A | 1/1994 | Weber et al. | |
| 5,308,335 A | 5/1994 | Ross et al. | |
| 5,312,337 A | 5/1994 | Flaherty et al. | |
| 5,318,540 A | 6/1994 | Athayde et al. | |
| 5,342,313 A | 8/1994 | Campbell et al. | |
| 5,346,476 A | 9/1994 | Elson | |
| 5,364,342 A | 11/1994 | Beuchat et al. | |
| 5,411,480 A | 5/1995 | Kriesel | |
| 5,433,710 A | 7/1995 | Van Antwerp et al. | |
| 5,452,033 A | 9/1995 | Balling et al. | |
| 5,492,534 A | 2/1996 | Athayde et al. | |
| 5,505,709 A | 4/1996 | Funderburk et al. | |
| 5,507,288 A | 4/1996 | Bocker et al. | 128/633 |
| 5,514,096 A | 5/1996 | Hiejima | |
| 5,533,389 A | 7/1996 | Kamen et al. | |
| 5,545,152 A | 8/1996 | Funderburk et al. | |
| 5,569,187 A * | 10/1996 | Kaiser | 604/67 |
| 5,573,342 A | 11/1996 | Patalano | |
| 5,575,770 A | 11/1996 | Melsky et al. | |
| 5,576,781 A | 11/1996 | Deleeuw | |
| 5,582,593 A | 12/1996 | Hultman | |
| 5,584,813 A | 12/1996 | Livingston et al. | |
| 5,630,710 A | 5/1997 | Tune et al. | |
| 5,637,095 A | 6/1997 | Nason et al. | |
| 5,643,213 A | 7/1997 | McPhee | |
| 5,647,853 A | 7/1997 | Feldmann et al. | |
| 5,660,728 A | 8/1997 | Saaski et al. | |
| 5,665,065 A | 9/1997 | Colman et al. | |
| 5,665,070 A | 9/1997 | McPhee | |
| 5,678,539 A | 10/1997 | Schubert et al. | |
| 5,685,844 A * | 11/1997 | Marttila | 604/65 |
| 5,685,859 A | 11/1997 | Kornerup | |
| 5,695,490 A | 12/1997 | Flaherty et al. | |
| 5,702,363 A | 12/1997 | Flaherty | |
| 5,704,520 A | 1/1998 | Gross | |
| 5,726,404 A | 3/1998 | Brody | |
| 5,726,751 A | 3/1998 | Altendorf et al. | |
| 5,741,228 A | 4/1998 | Lambrecht et al. | |
| 5,747,350 A | 5/1998 | Sattler | |
| 5,748,827 A | 5/1998 | Holl et al. | |
| 5,755,682 A | 5/1998 | Knudson et al. | |
| 5,776,103 A | 7/1998 | Kriesel et al. | |
| 5,779,676 A | 7/1998 | Kriesel et al. | |
| 5,785,681 A | 7/1998 | Indravudh | |
| 5,785,688 A | 7/1998 | Joshi et al. | |
| 5,797,881 A | 8/1998 | Gadot | |
| 5,800,397 A | 9/1998 | Wilson | |
| 5,800,405 A | 9/1998 | McPhee | |
| 5,810,015 A | 9/1998 | Flaherty | |
| 5,814,020 A | 9/1998 | Gross | |
| 5,839,467 A | 11/1998 | Saaski et al. | |
| 5,840,063 A | 11/1998 | Flaherty | |
| 5,845,218 A | 12/1998 | Altschul | |
| 5,848,991 A | 12/1998 | Gross et al. | |
| 5,851,197 A | 12/1998 | Marano et al. | |
| 5,858,005 A | 1/1999 | Kriesel | |
| 5,858,239 A | 1/1999 | Kenley | |
| D405,524 S | 2/1999 | Falk et al. | |
| 5,865,806 A | 2/1999 | Howell | |
| 5,871,470 A | 2/1999 | McWha | |
| 5,875,393 A | 2/1999 | Altschul et al. | |
| 5,886,647 A | 3/1999 | Badger et al. | |
| 5,897,530 A | 4/1999 | Jackson | |
| 5,906,597 A | 5/1999 | McPhee | |
| 5,911,716 A | 6/1999 | Rake et al. | |
| 5,919,167 A | 7/1999 | Mulhauser et al. | |
| 5,931,814 A | 8/1999 | Alex et al. | |
| 5,935,099 A | 8/1999 | Peterson et al. | |
| 5,954,058 A | 9/1999 | Flaherty | |
| 5,957,890 A | 9/1999 | Mann et al. | |
| 5,961,492 A | 10/1999 | Kriesel et al. | |
| 5,965,848 A | 10/1999 | Altschul et al. | |
| 5,983,094 A | 11/1999 | Altschul et al. | |
| 5,993,423 A | 11/1999 | Choi | |
| 5,997,501 A | 12/1999 | Gross et al. | |
| 6,019,747 A | 2/2000 | McPhee | |
| 6,024,539 A | 2/2000 | Blomquist | |
| 6,061,580 A | 5/2000 | Altschul et al. | |
| 6,071,292 A | 6/2000 | Makower et al. | |
| 6,144,847 A | 11/2000 | Altschul et al. | |
| 6,174,300 B1 | 1/2001 | Kriesel et al. | |
| 6,190,359 B1 | 2/2001 | Heruth | |
| 6,206,850 B1 | 3/2001 | O'Neil | |
| 6,244,776 B1 | 6/2001 | Wiley | |
| 6,375,638 B1 | 4/2002 | Nason et al. | |
| 6,520,936 B1 | 2/2003 | Mann | |
| 6,527,744 B1 | 3/2003 | Kriesel et al. | |

| | | | | |
|---|---|---|---|---|
| 6,554,798 | B1 * | 4/2003 | Mann et al. | 604/131 |
| 6,689,091 | B1 * | 2/2004 | Bui et al. | 604/67 |
| 6,692,457 | B1 | 2/2004 | Flaherty | |
| 2001/0056258 | A1 * | 12/2001 | Evans | 604/131 |
| 2004/0068224 | A1 | 4/2004 | Couvillion | |

FOREIGN PATENT DOCUMENTS

| | | |
|---|---|---|
| DE | 19920896 | 9/2000 |
| EP | 0342947 | 5/1989 |
| EP | 0319272 A2 | 6/1989 |
| EP | 0763369 | 3/1997 |
| EP | 0867196 | 3/1998 |
| EP | 0937475 | 8/1999 |
| EP | 1177802 A1 | 2/2002 |
| WO | WO81/01658 | 6/1981 |
| WO | WO86/06796 | 11/1986 |
| WO | WO98/00193 | 1/1998 |
| WO | WO98/01071 | 1/1998 |
| WO | WO99/10040 | 3/1999 |
| WO | WO00/19887 | 9/1999 |
| WO | WO99/56803 | 11/1999 |
| WO | WO99/62576 | 12/1999 |
| WO | WO0010628 | 2/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |
| WO | WO00/48112 | 8/2000 |
| WO | WO0/013580 | 9/2000 |
| WO | WO00/61215 | 10/2000 |
| WO | WO01/52727 | 1/2001 |
| WO | WO01/5663 | 8/2001 |
| WO | WO02/20073 | 8/2001 |
| WO | WO01/76684 | 10/2001 |
| WO | WO 02/20073 | 3/2002 |
| WO | WO02/26282 | 4/2002 |

OTHER PUBLICATIONS

Web-Site Brochure dated Dec. 20, 1999. Applied Medical Technology. "508 Pump Information". www.applied-medical.co.uk/508.htm.
Web-Site Brochure dated Jan. 4, 2000. "The Glucose Sensor". www.animascorp.com/sensor_f.html.
Web-Site Brochure dated Dec. 20, 1999. "The Animas R-1000 Insulin Pump". www.animascorp.com/pump_f_s.html.
Web-Site Brochure dated Dec. 20, 1999. "The Animas R-1000 Insulin Pump". www.animascorp.com/pump_f_f.html.
Web-Site Brochure dated Jan. 4, 2000. SOOIL-Homepage. "Portable Insulin Pump". www.sooil.com/intro2.htm.
Web-Site Brochure dated Jan. 4, 2000. SOOIL-Homepage. "Portable Insulin Pump". www.sooil.com/product2.htm.
Web-Site Brochure dated Jan. 4, 2000. SOOIL-Homepage. "Portable Insulin Pump". www.sooil.com/product3.htm.
Web-Site Brochure dated Jan. 4, 2000. SOOIL-Homepage. "Portable Insulin Pump". www.sooil.com/product4.htm.
User's Guide for Model 508 Insulin Pump, MiniMed, Aug. 2000, 145 pages.
European Patent Office, Communication Pursuant to Article 96(2) EPC in EPA No. 01968320.0, Jan. 21, 2005.
European Patent Office, Communication Pursuant to Article 96(2) EPC in EPA No. 01977472.8, Jul. 19, 2004.
European Patent Office, Communication Pursuant to Article 96(2) EPC in EPA No. 01987579.8, Jan. 26, 2005.
Australian Patent Office, Examiner's First Report on Patent Application No. 2001288575, Mar. 23, 2005.
Australian Patent Office, Examiner's First Report on Patent Application No. 2001296588, Mar. 16, 2005.
Australian Patent Office, Examiner's First Report on Patent Application No. 2002239709, May 18, 2005.
International Preliminary Examining Authority, International Search Report PCT/US03/03731, Jul. 2, 2003.
International Preliminary Examining Authority, Written Opinion PCT/US03/03731, Jun. 17, 2004.
International Preliminary Examining Authority, International Search Report PCT/US01/31089, May 20, 2002.
International Preliminary Examining Authority, Written Opinion PCT/US01/31089, Sep. 29, 2003.
International Preliminary Examining Authority, International Preliminary Examination PCT/US01/31089, Aug. 21, 2001.
International Preliminary Examining Authority, International Search Report PCT/US01/10933, Oct. 28, 2003.
International Preliminary Examining Authority, Written Opinion PCT/US01/10933, Apr. 11, 2003.
International Preliminary Examining Authority, International Preliminary Examination Report PCT/US01/10933, Oct. 28, 2003.
International Preliminary Examining Authority, International Search Report PCT/US01/27108, Apr. 3, 2002.
International Preliminary Examining Authority, Written Opinion PCT/US0127108, Apr. 16, 2003.
International Preliminary Examining Authority, International Preliminary Examination Report PCT/US01/27108, Nov. 4, 2003.
International Preliminary Examining Authority, International Search Report PCT/US02/05338, Dec. 18, 2002.
International Preliminary Examining Authority, International Preliminary Examination Report PCT/US02/05338, Mar. 3, 2003.
International Preliminary Examining Authority, International Search Report PCT/US02/28053, May 20, 2003.
International Preliminary Examining Authority, Written Opinion PCT/US02/28053, Dec. 3, 2003.
International Preliminary Examining Authority, International Preliminary Examination Report PCT/US02/28053, Dec. 9, 2004.
International Preliminary Examining Authority, International Search Report PCT/US03/09606, Oct. 20, 2003.
International Preliminary Examining Authority, International Preliminary Examination Report PCT/US03/09606, Dec. 16, 2003.
International Preliminary Examining Authority, International Search Report PCT/US03/09952, Aug. 12, 2003.
International Preliminary Examining Authority, International Preliminary Examination Report PCT/US03/09952, Jan. 20, 2004.
International Preliminary Examining Authority, International Preliminary Examination Report PCT/US03/12370, Dec. 15, 2003.
International Preliminary Examining Authority, International Preliminary Examination Report PCT/US03/12370, Feb. 11, 2004.
International Preliminary Examining Authority, International Search Report PCT/US03/16545, Oct. 6, 2003.

International Preliminary Examining Authority, International Preliminary Examination Report PCT/US03/16545, Feb. 23, 2004.

International Preliminary Examining Authority, International Search Report PCT/US03/28769, Aug. 12, 2004.

International Preliminary Examining Authority, International Preliminary Examination Report PCT/US03/28769, Aug. 12, 2004.

International Searching Authority, International Search Report PCT/US03/16640, Oct. 2, 2003.

International Searching Authority, International Preliminary Examination Report PCT/US03/16640, Feb. 25, 2004.

International Searching Authority, International Search Report PCT/US01/51285, Jun. 11, 2002.

International Preliminary Examining Authority, International Search Report PCT/US03/29019, Aug. 2, 2004.

International Preliminary Examining Authority, International Search Report PCT/US02/30803, Mar. 3, 2003.

International Preliminary Examining Authority, Written Opinion PCT/US02/30803, Aug. 26, 2003.

International Preliminary Examining Authority, Written Opinion PCT/US03/19756, Aug. 6, 2004.

International Searching Authority, International Search Report PCT/US03/19756, Mar. 10, 2004.

US 5,954,699, 09/1999, Jost et al. (withdrawn)

* cited by examiner

DEVICES, SYSTEMS AND METHODS FOR PATIENT INFUSION

CROSS-REFERENCE TO RELATED APPLICATIONS

This is a division of application Ser. No. 09/943,992, filed Aug. 31, 2001, now U.S. Pat. 6,740,059 claims priority to provisional U.S. patent application Ser. No. 60/231,476, filed on Sep. 8, 2000, which is assigned to the assignee of the present application and incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids to a mammalian patient.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and syringe, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge or syringe, and use electro-mechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling of these devices or their reservoirs can be difficult and require the patient to carry both the intended medication as well as filling accessories when traveling or even just going to work. The accuracy and safety requirements of these devices are extremely important, based both on the medicine being delivered and the condition of the patient. Therefore, the devices require specialized care, maintenance and cleaning to assure proper functionality and safety for their intended long term use. The devices are usually sold for $4,000 to $6,000 requiring maintenance of the device for four or more years to justify the expenditure. Also due to the cost, replacement devices are not easily available or practical. Any damage to the device, such as that caused by it being dropped, result not only in the costs of repair or replacement, but also in a period of discontinued therapy. The high cost of the device is a concern of healthcare providers who approve and prescribe the use of the device, limiting the expansion of the patient populations and therapies for which the devices can be used.

Clearly, therefore, there is a need for a programmable and adjustable infusion system that is precise and reliable and can offer clinicians and patients a small, low cost, light weight, simple to use alternative for parenteral delivery of liquid medicines.

SUMMARY OF THE INVENTION

The applicant has determined that a sophisticated ambulatory infusion device that can be programmed to reliably deliver variable flow profiles of liquid medications, yet is small, light weight and low cost, is needed. Smaller and lighter devices are easier to carry and are more comfortable for the patient, even allowing the device to be adhesively attached to the patient's skin similar to a transdermal patch. An inexpensive device allows greater flexibility in prescribing the device for use by reducing the financial burden on healthcare insurance providers, hospitals and patient care centers, as well as patients themselves. In addition, low cost devices make more practical the maintenance of one or more replacement devices. If the primary device is lost or becomes dysfunctional, availability of the replacement avoids costly expedited repair and down time.

Aspects of the present invention will enable cost reductions significant enough to make the entire device disposable in nature, being replaced as frequently as every two to five days. A disposable device allows the medication to be prefilled by the manufacturer and does not need the routine cleaning and maintenance required by long term devices, greatly simplifying use for the patient. Similar to disposable cameras which have become increasingly popular in recent years, another benefit is that each time a disposable fluid delivery device is purchased, it is the latest or state of the art technology. Long term use devices may be outdated in a year when a new version is available from the manufacturer, just twenty five percent of the life expectancy of the original device.

The present invention, therefore, provides a device for delivering fluid to a patient, including an exit port assembly adapted to connect to a transcutaneous patient access tool, a dispenser for causing fluid from a reservoir to flow to the exit port assembly, a local processor connected to the dispenser and programmed to cause a flow of fluid to the exit port assembly based on flow instructions from a separate, remote control device, and a wireless receiver connected to the local processor for receiving the flow instructions from a separate, remote control device and delivering the flow instructions to the local processor. The device also includes a housing containing the exit port assembly, the dispenser, the local processor, and the wireless receiver. The housing is free of user input components for providing flow instructions to the local processor in order to reduce the size, complexity and costs of the device, such that the device lends itself to being disposable in nature.

According to one aspect of the present invention, the flow instructions cause a predetermined rate of fluid flow for a predetermined period. According to another aspect, the predetermined rate of fluid flow comprises a basal rate.

According to another aspect of the present invention, the flow instructions cause a predetermined volume of fluid to flow for a predetermined period. According to an additional aspect, the predetermined volume comprises a bolus volume.

According to an additional aspect, the device includes a least one user interface component accessible from an exterior of the housing for causing a predetermined volume of fluid to flow for a predetermined period, independently of the local processor. According to a further aspect, the device includes a least one user interface component accessible from an exterior of the housing for occluding flow to the exit port assembly.

According to another aspect of the present invention, the device includes a power supply connected to the local processor. According to an additional aspect, the device includes a transmitter connected to the local processor for transmitting information from the local controller to a separate, remote control device. According to still a further aspect, the housing is free of user output components for providing information from the local processor. According to a further aspect, the exit port assembly includes a tubular member for transcutaneously entering a patient. According to still a further aspect, the device includes a reservoir.

The present invention also provides a system including a fluid delivery device as described above, and further including a separate, remote control device including a remote processor, user input components connected to the remote processor for allowing a user to provide instructions to the remote controller, and a transmitter connected to the remote controller for transmitting the instructions to the receiver of the fluid delivery device. Thus, the remote controller allows a user, such as a patient, nurse or doctor, to remotely program the fluid delivery device to provide a desired infusion of fluid into the patient.

The present invention further provides another device for delivering fluid to a patient, including an exit port assembly adapted to connect to a transcutaneous patient access tool, a dispenser for causing fluid from a reservoir to flow to the exit port assembly, a local processor connected to the dispenser and programmed to cause fluid flow to the exit port assembly based upon flow instructions. The local processor is also programmed to provide flow information, and a wireless transmitter is connected to the local processor for transmitting the flow information to a separate, remote control device. A housing contains the exit port assembly, the dispenser, the local processor, and the wireless transmitter, and is free of user output components for providing the flow information from the local processor to a user.

These aspects of the invention together with additional features and advantages thereof may best be understood by reference to the following detailed descriptions and examples taken in connection with the accompanying illustrated drawings.

BRIEF DESCRIPTION OF THE DRAWINGS

Like reference characters designate identical or corresponding components and units throughout the several views.

DETAILED DESCRIPTION OF THE PREFERRED EMBODIMENTS

Set forth hereinbelow are detailed descriptions of certain embodiments and examples of fluid delivery devices, systems and kits, constructed in accordance with the present invention, as well as methods for using the devices, systems and kits. The types of liquids that can be delivered by the fluid delivery devices, systems and kits of the present invention include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery devices, systems and kits of the present invention might be used to treat include diabetes, cardiovascular disease, pain, chronic pain, cancer, AIDS, neurological diseases, Alzheimer's Disease, ALS, Hepatitis, Parkinson's Disease or spasticity.

Figure 1:
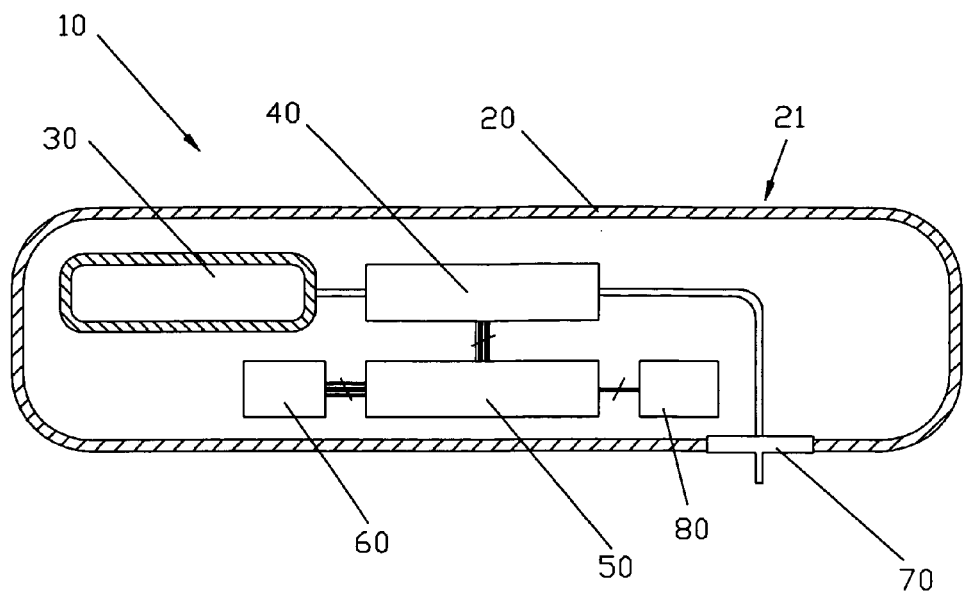
FIG. 1 is a sectional side view of a first exemplary embodiment of a fluid delivery device in accordance with this invention.
Figure 2:
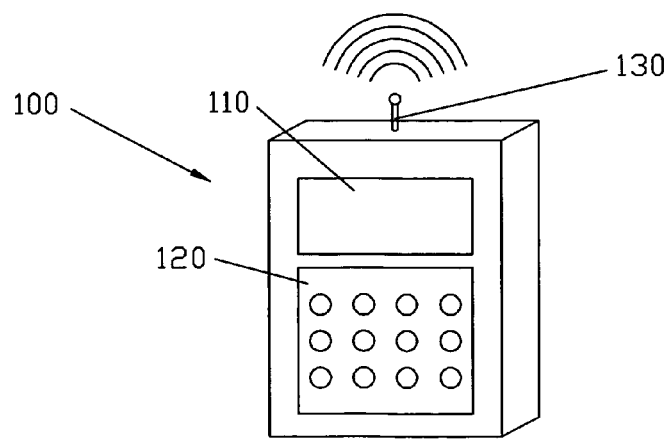
FIG. 2 is a perspective view of an exemplary embodiment of a remote control device in accordance with this invention for use with the fluid delivery device of FIG. 1.

In FIG. 1, there is illustrated, generally at 10, a fluid delivery device according to the invention. The device 10 generally includes an exit port assembly 70 adapted to connect to a transcutaneous patient access tool, a dispenser 40 for causing fluid from a reservoir 30 to flow to the exit port assembly, a processor or electronic microcontroller (hereinafter referred to as the "local" processor) 50 connected to the dispenser and programmed to cause a flow of fluid to the exit port assembly based on flow instructions from a separate, remote control device (an example of which is shown in FIG. 2), and a wireless receiver 60 connected to the local processor for receiving the flow instructions from the separate, remote control device and delivering the flow instructions to the local processor. The device also includes a housing 20 containing the exit port assembly 70, the dispenser 40, the local processor 50, and the wireless receiver 60. The housing 20 is free of user input components, such as external buttons connected to the processor 50, for providing flow instructions to the local processor 50 in order to reduce the size, complexity and costs of the device 10, such that the device lends itself to being small and disposable in nature.

In the exemplary embodiment of FIG. 1, the device 10 also includes a reservoir 30 contained within the housing 20 and connected to the dispenser 40. The reservoir 30 is provided with a collapsible design such as a metal bellows or is made of a collapsible material such as a silicone elastomer. The volume of the reservoir 30 is chosen to best suit the therapeutic application of the fluid delivery device 10 impacted by such factors as available concentrations of medicinal fluids to be delivered, acceptable times between refills or disposal of the fluid delivery device 10, size constraints and other factors. For treatment of Type I diabetics, for example, a reservoir of less than 5 ml, and preferably 2 to 3 ml, is appropriate.

The local processor 50 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the dispenser at the needed time intervals. In the exemplary embodiment of FIG. 1, a power supply 80, such as a battery or capacitor, is included and supplies power to the local processor 50.

When the local processor 50 activates the dispenser 40, a specific amount of fluid exits the fluid delivery device 10 via the exit port assembly 70. The exit port assembly 70 can include elements to transcutaneously enter the patient, such as a needle or soft cannula, or can be adapted to connect to a standard infusion device that includes transcutaneous delivery means.

As shown, the housing 20 is free of user input components for providing flow instructions to the local processor 50, such as electromechanical switches or buttons on an outer surface 21 of the housing, or interfaces otherwise accessible to a user to adjust the programmed flow rate through the local processor 50. In order to program, adjust the programming of, or otherwise communicate user inputs to the local processor 50, the fluid delivery device 10 includes the wireless communication element, or receiver 60 for receiving the user inputs from a separate, remote control device, such as the separate, remote control device 100 of FIG. 2. Signals can be sent via a communication element (not shown) of the remote control device 100, which can include or be connected to an antenna 130, shown in FIG. 2 as being external to the device 100.

The remote control device 100 has user input components, including an array of electromechanical switches, such as the membrane keypad 120 shown. The control device 100 also includes user output components, including a visual display, such as a liquid crystal display (LCD) 110. Although not shown in FIG. 2, the remote control device 100 has its own processor (hereinafter referred to as the "remote" processor) connected to the membrane keypad 120 and the LCD 110. The remote processor is programmed to receive the user inputs from the membrane keypad 120 and translate the user inputs into "flow" instructions for transmission to the fluid delivery device 10, and is programmed to send user outputs to the LCD 110.

A user, such as a patient or a clinician, can thus program the fluid delivery device 10 by entering information into the remote control device 100, which then downloads information to the receiver 60 of the device 10 with each key stroke or button pressed or in a batch mode of multiple key strokes. Complex flow algorithms, requests for bolus delivery and other desired infusions of the medicinal fluid can be accomplished by entering information into the remote control device 100, which is then transmitted to the fluid delivery device 10. The communication can be confirmed as acceptable by the local processor 50 of the fluid delivery device 10 by using one or more features such as standard handshaking protocols, redundant transmissions and other communication confirmation methods, as are known to those skilled in the art.

The lack of user interfaces, such as electromechanical switches on the fluid delivery device 10, results in substantial reductions in the cost, the size, and the weight of the device 10. The lack of user interfaces also allows the housing outer surface 21 of the device 10 to be relatively smooth, thereby simplifying cleaning and preventing jewelry or clothing items such as sweaters from catching on the device. Since the remote control device 100 also includes a visual display 110, the fluid delivery device 10 can be void of an information screen, further reducing cost, size and weight. Lack of user interfaces, such as electromechanical switches and information screens, greatly simplifies the design of the fluid delivery device 10 and allows the device 10 to be made more flexible and resistant to damage.

Figure 3:
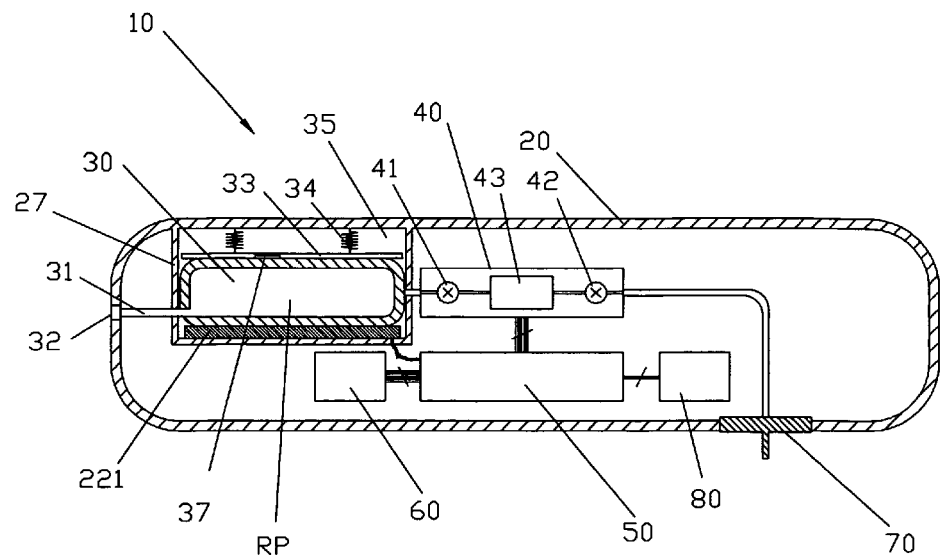
FIG. 3 is a sectional side view of a second exemplary embodiment of a fluid delivery device in accordance with this invention.

FIG. 3 shows another exemplary embodiment of the fluid delivery device 10 of the present invention wherein the reservoir 30 is made of a flexible material and is enclosed in a reservoir chamber 35, which can be defined by the housing 20 and housing reservoir walls 27. The flexible reservoir 30 is placed in compression by a compressing member 33 and compressing springs 34, which are positioned between the compressing member 33 and the housing 20. The compressed, flexible reservoir 30 causes fluid inside the reservoir 30 to be at a pressure above atmospheric pressure. In a preferred embodiment, a cross sectional area of the compressing member 33 approximates a cross sectional area of the reservoir 30.

Alternatively, the housing 20 may include a flexible cantilever beam that contacts the reservoir 30 creating a pressure within the reservoir 30 above atmospheric pressure. In another alternative, the reservoir chamber 35 may be sealed and filled with a gas, or a vapor-plus-fluid mixture, to place the fluid within the reservoir 30 under pressure above atmospheric pressure. The gas can be air, and the vapor-plus-fluid mixture can be Freon. The Freon vapor-plus-fluid mixture provides the design advantage of near constant pressure if the fluid delivery device 10 is maintained at near constant temperature. In still another alternative embodiment, the amount of gas placed in a sealed reservoir chamber 35 may be chosen such that the reservoir 30 pressure is equal to or less than atmospheric for the entire full to empty conditions of the reservoir 30. If the fluid in the reservoir 30 is maintained at a pressure equal to or below atmospheric, then the dispenser 40 is provided in the form of a pump, such as a peristaltic drive pump, for pumping fluid from the reservoir 30 to the outlet port assembly 70.

The reservoir 30 may be prefilled by the device manufacturer or a cooperating drug manufacturer, or may include external filling means consisting of a fill assembly 31. If the fluid delivery device 10 is prefilled by the manufacturer, the local processor 50 can be provided with memory containing various information regarding the prefilled drug including but not limited to, the type or name and the concentration and volume of the fluid.

The fill assembly 31 can include a needle insertion septum 32. The reservoir 30 and other fluid path components may be placed in a vacuum during the final manufacturing process to simplify filling and priming of the fluid delivery device 10 for the patient. Needle insertion septum 32 may be constructed of a resealing elastomer such as silicone that allows a needle to puncture septum to add fluid to the reservoir 30, yet reseal after the needle is withdrawn. An alternative to the needle insertion septum 32 is a standard fluid connection, such as a Luer connector, which can be affixed to the fill assembly 31 in combination with a one way valve such as a duck bill valve (not shown). The patient could attach a syringe filled with the liquid medication to the Luer connector and fill the fluid delivery device 10. The fill assembly 31 may be designed so that the patient can fill the fluid delivery device 10 one time only, such as by having the Luer connection break off when the syringe is removed.

The dispenser 40 is connected in fluid communication with the reservoir 30. When the device 10 is provided with a pressurized reservoir 30, as shown in exemplary embodiment of FIG. 3, the dispenser can include an inlet valve 41 connected to the reservoir, and outlet valve 42 connected to the exit port assembly 70, and an accumulator 43 connected between the inlet valve and the outlet valve. Since the fluid in the reservoir 30 is maintained at a pressure above atmospheric pressure, opening of the inlet valve 41 allows the accumulator to fill to the reservoir pressure, after which the inlet valve is 41 is closed. At the proper time, as determined by the local processor 50 programming and instructions received from the remote control device, the outlet valve 42 can be opened to dispense fluid to the exit port assembly 70, which is at the pressure of the patient, or atmospheric pressure. The accumulator 43 will then be at atmospheric pressure, and the outlet valve 42 can be closed, ready for another repeat cycle.

The dispenser 40 of the exemplary embodiment of FIG. 3 does not create a driving or pumping force on the fluid passing therethrough, but rather acts as a metering device, allowing pulses of fluid to pass from the pressurized reservoir 30, through the dispenser 40, to the exit port assembly 70 at atmospheric pressure. The inlet valve 41 and the outlet valve 42 of the dispenser 40 are controlled by the local processor 50, which includes electronic programming, controls and circuitry to allow sophisticated fluid delivery programming and control of the dispenser 40.

Figures 3A, 3B:
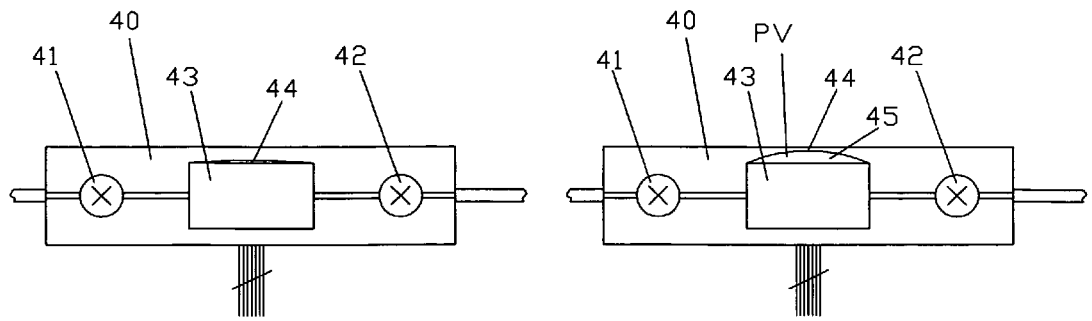
FIG. 3a is an enlarged partial sectional view of a dispenser for the device of FIG. 3, shown with an accumulator empty and ready to be filled upon an inlet valve being opened.
FIG. 3b is an enlarged sectional view of the dispenser for the device of FIG. 3, shown with the accumulator filled and ready to dispense a pulse of fluid upon an outlet valve being opened.

FIG. 3a shows the dispenser 40 with the accumulator 43 at atmospheric pressure. An accumulator membrane 44 is shown in its non-distended state, caused by atmospheric pressure only. Inlet valve 41 is closed, and outlet valve 42 may be open or closed, but must have been opened since the last time inlet valve 41 was opened. FIG. 3b shows the condition where outlet valve 42 is closed, and inlet valve 41 has been opened. Because of the elevated pressure of the fluid from the reservoir 30, the accumulator membrane 44 is distended, thus increasing the volume of accumulator 43 by an accumulator volume 45. After the inlet valve 41 is closed, the outlet valve 42 can be opened, to dispense the accumulator volume 45 and allow the accumulator membrane 44 to retract to the position shown in FIG. 3a.

The inlet valve 41 and the outlet valve 42 of the dispenser 40 and the local processor 50 are designed to prevent both valves from being opened at the same time, precluding the reservoir 30 to ever flow directly to the exit port assembly 70. The prevention of both valves opening at the same time is critical and can be accomplished via mechanical means, electrical means, or both. The prevention can be accomplished in the dispenser 40 design, the local processor 50 design, or both.

The dispenser 40 shown in FIGS. 3, 3a and 3b dispenses finite pulses of fluid volume, called pulse volume (PV), with each activation. The PV is determined by the properties, materials and construction of the accumulator 43 and the accumulator membrane 44. PV's delivered by infusion devices are typically chosen to be small relative to what would be considered a clinically significant volume. For insulin applications at a concentration of 100 units per ml, a PV of less than 2 microliter, and typically 0.5 microliter, is appropriate. If the fluid delivery device 10 is programmed via the remote control device 100 to deliver 2 units an hour, the dispenser will deliver 40 pulses an hour, or a pulse every 1.5 minutes. Such pulsitile flow is considered continuous if the PV is small enough. Other drugs or concentrations may permit a much larger PV. Various flow rates are achieved by adjusting the time between pulses. To give a fixed volume or bolus, multiple pulses are given in rapid succession until the bolus volume is reached.

The PV may not always be constant enough to be within the accuracy requirements of the fluid delivery device 10. One factor impacting the PV is reservoir pressure. The fluid delivery device 10 may include means for monitoring reservoir pressure (RP) and adjust the timing between pulses to achieve the desire flow pattern. An example of such compensation would be to decrease time between pulses as the PV decreases to maintain the programmed flow rate. Means for monitoring such parameters as reservoir pressure RP are described below. An alternative to monitoring reservoir pressure is monitoring the volume of the reservoir 30. Each time a pulse or series of pulses are delivered, a measurement of reservoir volume can indicate whether a proper amount of fluid has been delivered, both for individual pulses and cumulative pulses. The system could also be designed to compensate fluid flow as errors are detected. An example of a reservoir volume transducer means is also described below.

The communication element 60 preferably receives electronic communication from the remote control device 100 using radio frequency or other wireless communication standards and protocols. The information transferred includes codes or packets of codes that the local processor 50 uses to confirm that the information was received correctly, similar to the way standard telephone modem communication is performed. More sophisticated codes can be included to allow the information to be self-corrected or pinpoint the area of bad information. In an even more preferred embodiment, the communication element 60 is a two-way communication element, including a receiver and a transmitter, for allowing the fluid delivery device 10 to send information back to the remote control device 100. In such an embodiment, the remote control device 100 also includes an integral communication element 60 comprising a receiver and a transmitter, for allowing the remote control device 100 to receive the information sent by the fluid delivery device 10.

The power supply 80 can be integrated into the fluid delivery device 10 and not accessible to a user. In an alternative embodiment, however, the power supply 80 can be replaceable, e.g., a replaceable battery. In another embodiment, the power supply 80 can comprise an integrated battery or capacitor, for low power components of the device 10 such as the electronic memory, and a user-inserted battery for powering the remainder of the device 10. Other components that may require electrical energy are the communication element 60, the dispenser 40, and other components such as sensors or transducers.

As shown in FIG. 3, the device can include sensors or transducers such as a reservoir volume transducer 37. A similar transducer is described in U.S. Pat. No. 5,533,389 to Kamen et al. FIG. 3 also shows a pressure transducer 221, located on the housing reservoir walls 27 and in contact with a portion of the reservoir 30. The pressure transducer 221 may consist of force sensing resistor technology such as that manufactured by Interlink, Inc. of Camarillo, Calif. Reservoir transducer 37 or pressure transducer 221 can transmit information to local processor 50 to indicate how and when to activate the dispenser 40, or to indicate other parameters determining flow, as well as conditions such as the reservoir 30 being empty or leaking, or the dispensing of too much or too little fluid from the reservoir, etc.

Figure 4:
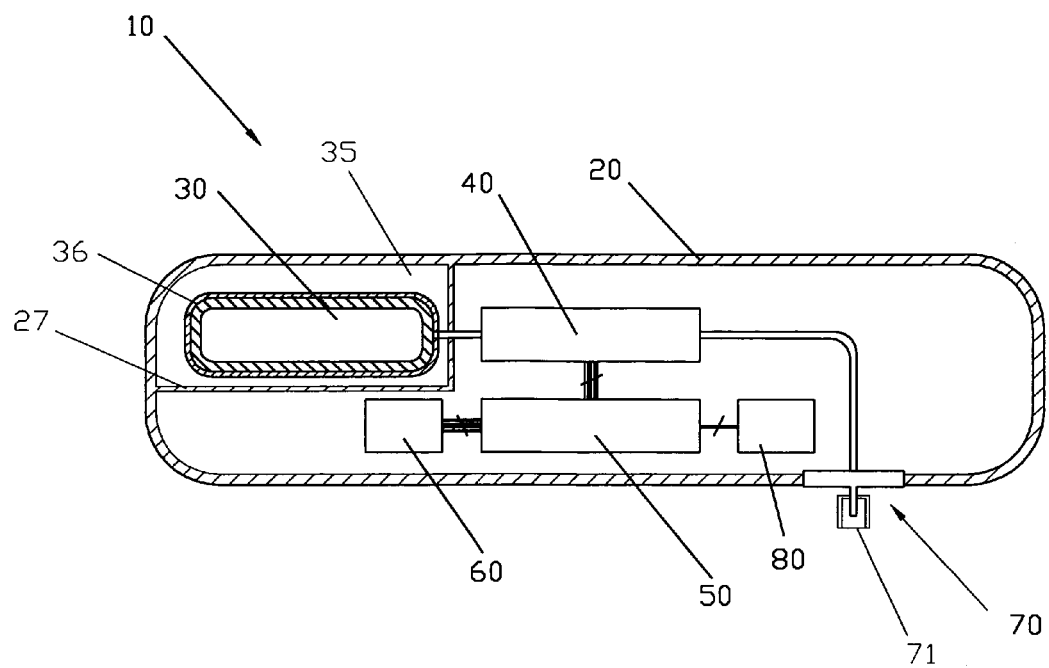
FIG. 4 is a sectional side view of a third exemplary embodiment of a fluid delivery device in accordance with this invention.

FIG. 4 shows another exemplary embodiment of the fluid delivery device 10 including an elastic sock 36 for compressing the reservoir 30 to a pressure above atmospheric pressure. The reservoir sock 36, constructed of an elastic material, has a very small unexpanded internal volume, no larger than the volume of reservoir 30 in its empty state. The reservoir sock 36 expands to support reservoir 30 when full, and elastically compresses until reservoir 30 is fully empty. Alternatively, the elastic reservoir 30 can be provided with a very small internal volume when empty, typically less than 100 microliters, and that expands during the fill process, creating a pressure within the reservoir greater than atmospheric pressure until the reservoir 30 is again empty, thereby obviating the need for the reservoir sock 36. The fluid delivery device 10 of FIG. 4 also includes a Luer connector 71 for attaching a standard transcutaneous fluid delivery set to the exit port assembly 70.

Figure 4A:
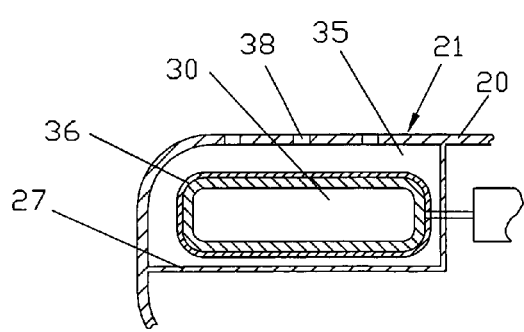
FIG. 4a is an enlarged sectional side view of a reservoir chamber of the device of FIG. 4.
Figure 4B:
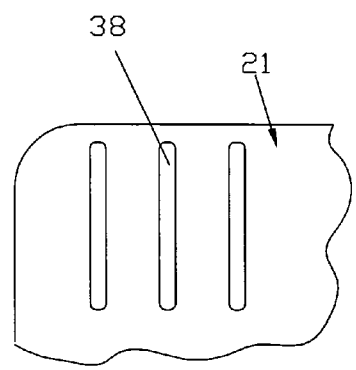
FIG. 4b is an enlarged bottom plan view of a portion of the reservoir chamber of the device of FIG. 4.

Since the fluid delivery device 10 may be worn close to or even attached to the body of a mammalian patient, it may be desired to prevent the temperature of the fluid in the reservoir 30 from elevating toward the body temperature of the patient. In one embodiment, the reservoir chamber 35 can be sealed and placed in a vacuum, similar to construction of a thermos bottle. The internal surface of the reservoir chamber 35 can be coated with reflective material, also similar to a thermos bottle. Alternatively, the chamber 35 can be filled with insulating material such as a low thermal conductance foam, with sufficient cavity size to allow the reservoir 30 to expand to a maximum fill capacity. Shown in FIGS. 4a and 4b are venting holes 38, placed through the housing 20 and housing outer surface 21 in the area of reservoir chamber 35 on the side of the device 10 away from the skin of the patient. The venting holes 38 allow the reservoir chamber 35 to vent to ambient temperature and thus help cool the reservoir 30.

Figure 5:
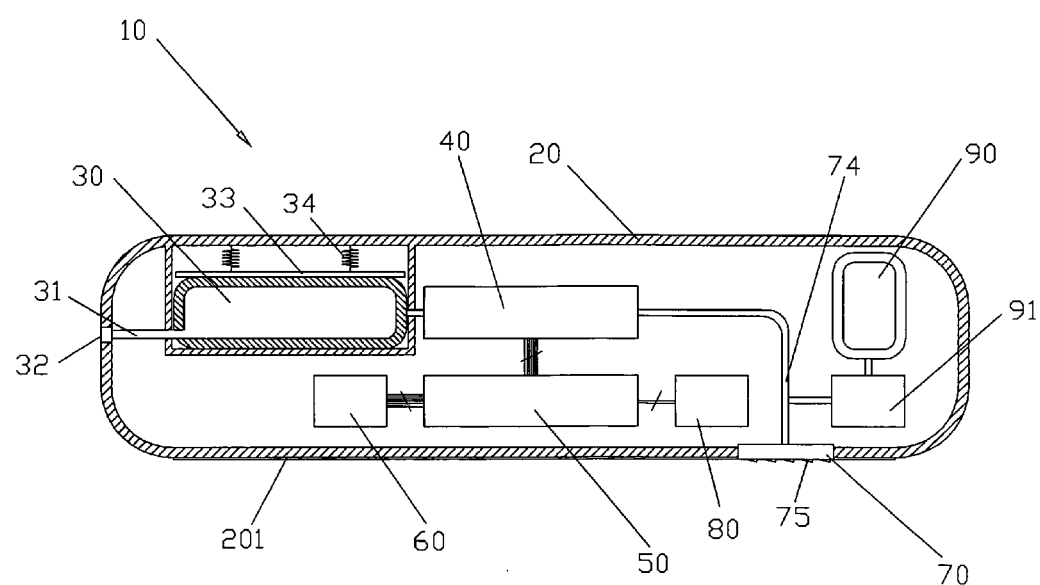
FIG. 5 is a sectional side view of a fourth exemplary embodiment of a fluid delivery device in accordance with this invention.

FIG. 5 shows another exemplary embodiment of the fluid delivery device 10 that includes a second reservoir 90 in fluid communication with a second dispenser 91. The additional reservoir 90 can be filled during the manufacturing process or can include filling means similar to the fill assembly 31. The additional dispenser 91 may include a separate controller, or can be controlled by the same local processor 50. The additional dispenser 91 connects distally to tubing lumen 74 extending between the main dispenser 40 and the exit port assembly 70. Similar to the main dispenser 40, the additional dispenser 91 is designed and controlled to prevent free flow of fluid from the additional reservoir 90 to the exit port assembly 70.

The second reservoir 90 may be filled with a drug different from the drug in the main reservoir 30, a diluent of the drug in the main reservoir 30 or any inert substance. The fluid from the additional reservoir 90 may be administered to dilute the fluid dispensed from the main reservoir 30, to provide more sophisticated or additive therapies, or even to maintain patency of the transcutaneous fluid path by flowing an inert substance at a more frequent rate then the intended infusion of the fluid in the main reservoir 30.

Figure 5A:
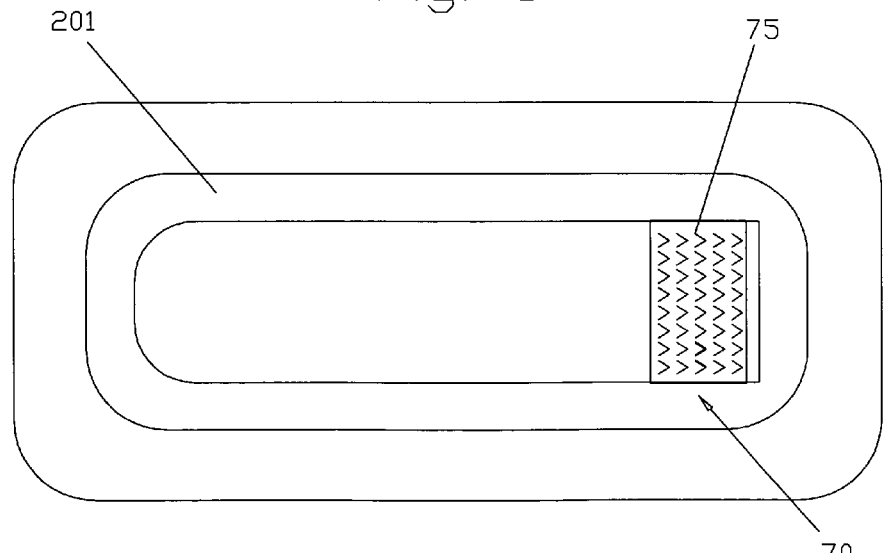
FIG. 5a is a bottom plan view of the device of FIG. 5.

Referring also to FIG. 5a, the device also includes a transcutaneous patient access tool comprising transcutaneous micropenetrators 75 connected to the exit port assembly 70. The transcutaneous micropenetrators 75 include a series of micro-needles or other micropenetrators that allow fluid to transcutaneously enter the body of the patient without standard needles. Similar transcutaneous micropenetrators are shown, for example, in U.S. Pat. No. 5,983,136 to Kamen et al.

The device 10 further includes an adhesive layer 201 on the outer surface 21 of the housing 20 for securing the device 10 directly to the skin of a patient. The adhesive layer is preferably provided in a continuous, oval shape encircling the exit port assembly 70 in order to provide a protective seal around the penetrated skin. The housing adhesive layer 201 can consist of material such as that used in bandages or electro surgery return pads such as those manufactured by the Valley Lab division of Tyco/U.S. Surgical.

Figure 6:
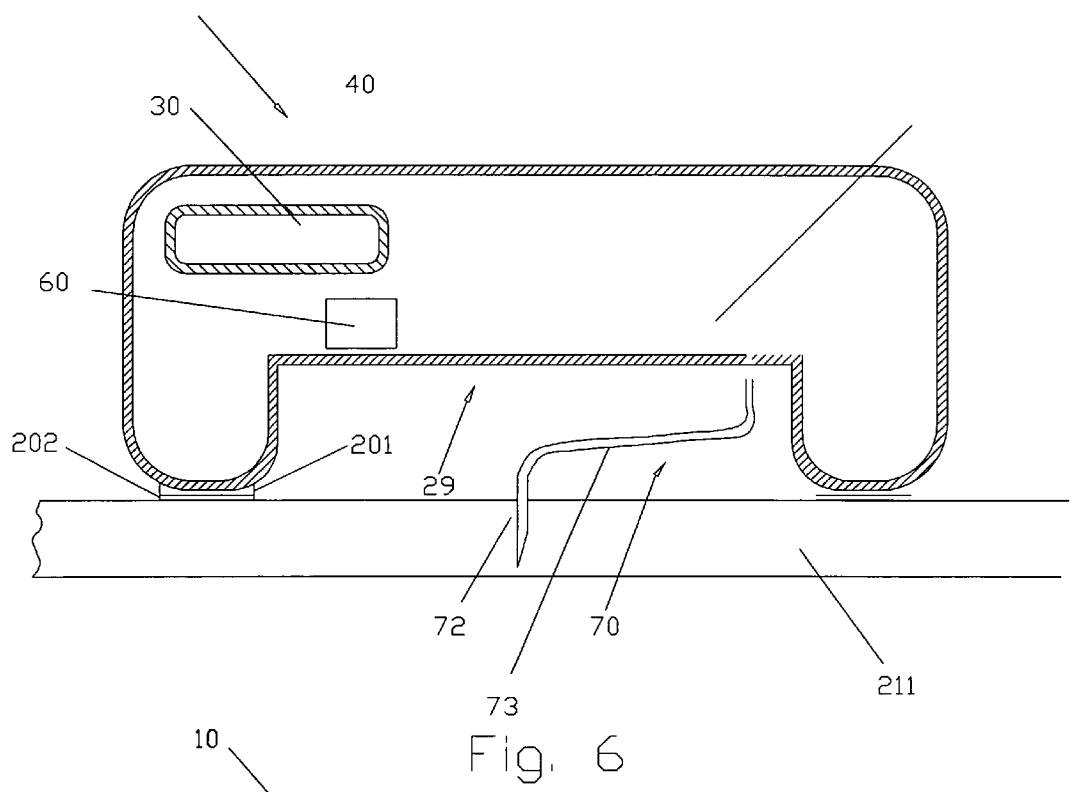
FIG. 6 is a sectional side view of a fifth exemplary embodiment of a fluid delivery device shown positioned on an outer surface of skin and subcutaneous tissue of a patient.
Figure 6A:
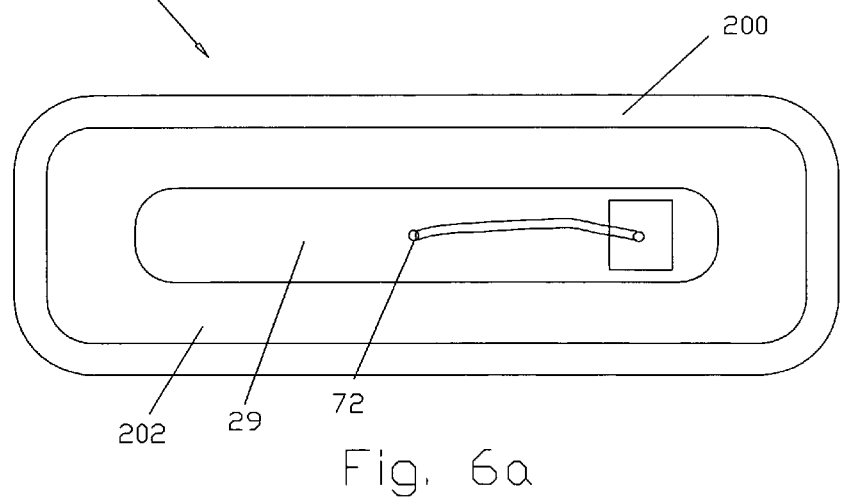
FIG. 6a is a bottom plan view of the device of FIG. 6.

FIGS. 6 and 6a show another exemplary embodiment of the fluid delivery device 10 including a housing 200 having a recessed surface 29 for creating an air pocket between the fluid delivery device 10 and the skin 210 of a patient. The device 10 also includes a secondary adhesive layer 202 attached to the first adhesive layer 201, which is attached to the bottom surface of the housing 200 surrounding the recessed surface 29. The secondary adhesive layer 202 allows the device 10 to be attached, removed and attached again to a patient. When first attached, the secondary adhesive layer 202 adheres to the skin 210. Upon removal of the device 10, the secondary adhesive layer 202 can be removed from the first adhesive layer 201, and the fluid delivery device 10 can then be reattached to the skin 210 using the adhesive layer 201.

A needle connection tubing 73 terminating in a skin penetrating cannula 72 is shown connected to the exit port assembly 70. The needle connection tubing 73 is flexible, allows various placements and can be reinforced to prevent kinking. Reinforcement can be accomplished through choice of materials and ratio of wall thickness to inner diameter, or the tubing 73 can be reinforced with an internal wire coil. The skin penetrating cannula 72 can be a rigid member, such as a needle, or can be flexible. The skin penetrating cannula 72 is inserted through the skin 210 prior to attaching the fluid delivery device 10 to the skin 210 and may be inserted using a needle insertion assistance mechanism. Such a needle insertion assistance mechanism may be integrated into the fluid delivery device 10, or can be supplied as a separate mechanism. FIG. 6 shows the cannula 72 entering through the surface of the skin 210 and entering subcutaneous tissue 211. Once the fluid delivery device 10 is attached to the skin 210, the needle connecting tube 73 remains relatively stable due to the direct connection between the device 10 and the skin 210. This stability helps prevent kinking of the tubing 73 and resultant occlusion, which is common to other ambulatory devices.

Figure 7:
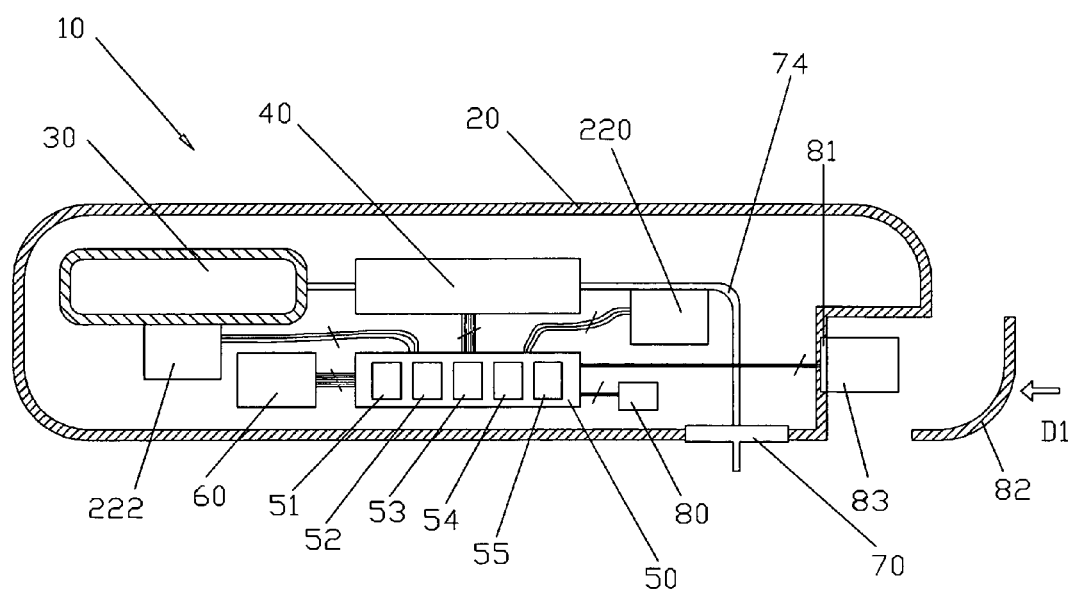
FIG. 7 is a sectional side view of a sixth exemplary embodiment of a fluid delivery device in accordance with the present invention.

FIG. 7 shows another exemplary embodiment of the fluid delivery device 10 including sensors providing feedback to the local processor 50, an electronic assembly for the various electronic devices and an optional second power supply 83. The sensors include a volume sensor 222, for example, provided in proximity with the reservoir 30 and an occlusion sensor 220 in proximity with the exit port tubing lumen 74.

The microcontroller 50 can include a microprocessor 51, memory 52, an electronic clock oscillator 53, an analog-to-digital converter 54 and a multiplexer 55. Also shown in FIG. 7 is the optional secondary power source 83, attached by the user to a battery connector 81 connected to the microcontroller 50. A battery door 82 is removed for insertion of the battery 83 and then reattached by sliding the door in direction D1 to the housing 20 of the fluid delivery device 10. In a preferred embodiment, the power supply 80 provides electrical power for memory retention and low power electronics only, while the secondary power source 83 provides electrical power for higher consumption components of the device 10, such as the dispenser 40. Both the power supply 80 and the secondary power source 83 may be consumer batteries, such as alkaline or nickel cadmium batteries, or other energy storage devices such as a capacitor. Additionally, both the power supply 80 and the secondary power source 83 may be rechargeable power sources.

Figure 8:
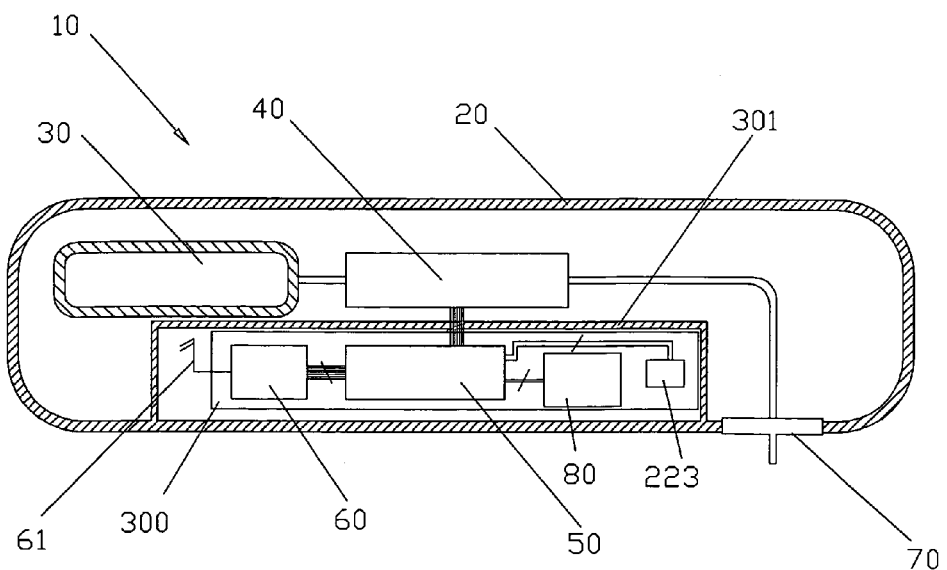
FIG. 8 is a sectional side view of a seventh exemplary embodiment of a fluid delivery device in accordance with the present invention.

FIG. 8 shows another exemplary embodiment of the fluid delivery device 10 including an electronic module 300 including the local processor 50 and other electronic devices in a modular subassembly, which simplifies manufacture, provides protection from water or other fluid damage, and provides shielding and protection from electromagnetic interference and static discharge. Attached to the electronic module 300 and connected to the communication element 60 is an optional antenna 61 to enhance transmitting of signals from the fluid delivery device 10 via the communication element 60. Alternatively, antenna 61 may be integrated into electronic module 300.

The device of FIG. 8 includes an alarm transducer 223, such as a beeper or vibration device, which is also integrated into the electronic module 300. The electronic module 300 is shown encapsulated by an electronic module housing 301, which is a portion of the housing 20. The electronic module housing 301 can easily be made to be waterproof, potentially by encapsulating the entire assembly in potting material, and can be protected with shielding material or coating for the electronic module 300 to resist electromagnetic interference and electrostatic discharge without having to encapsulate the entire internal portion of the fluid delivery device 10. Alternatively, the housing 20, in the portion surrounding the electronic module 300 can be shielded or made waterproof, potentially by using a gasket material. The optional antenna 61, which can be included internal or external to the shielding material, is shown as external. The electronic module 300 may include a microprocessor, logic circuitry, read only memory, writeable memory, random access memory, analog to digital conversion circuitry, a multiplexer, the power supply 80, resistors, capacitors, semiconductor components, programmable gate arrays, operational amplifiers and various other analog and digital electronic components.

Figure 8A:
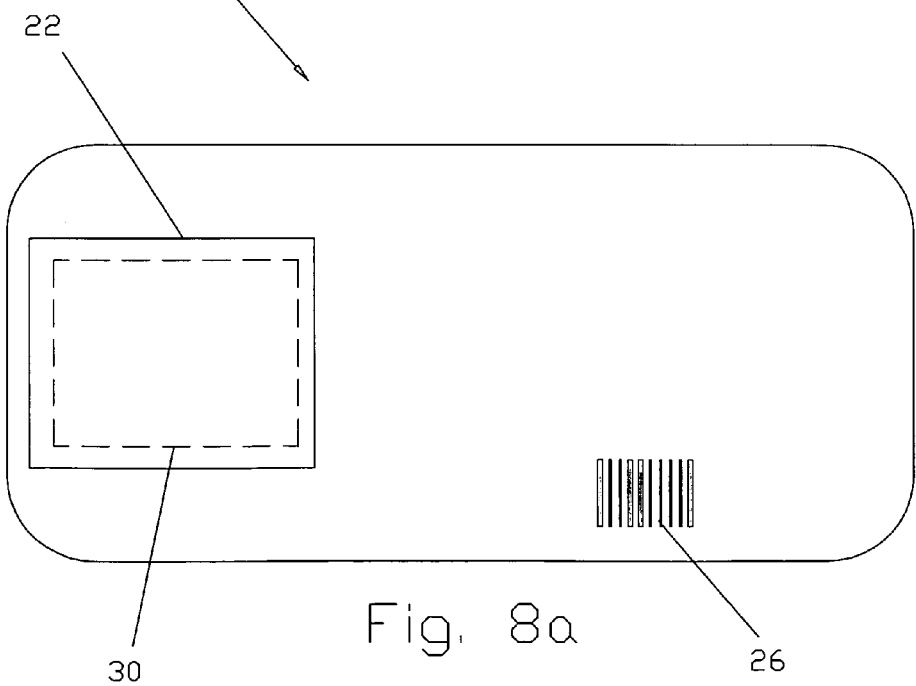
FIG. 8a is a top plan view of the device of FIG. 8.

FIG. 8a shows a transparent window 22 included in the housing 20 of the fluid delivery device 10 of FIG. 8, which allows a user to visually inspect the reservoir 30. Also shown is an information barcode 26, which has information that can be read by a remote control device 100 provided with a barcode scanner. Information on the barcode 26 can include amount, type and concentration of drug contained in the reservoir, the device manufacturer and serial number, and expiration dates, and various other pieces of information relative to infusion of liquid medicines into mammalian patients.

Figure 9:
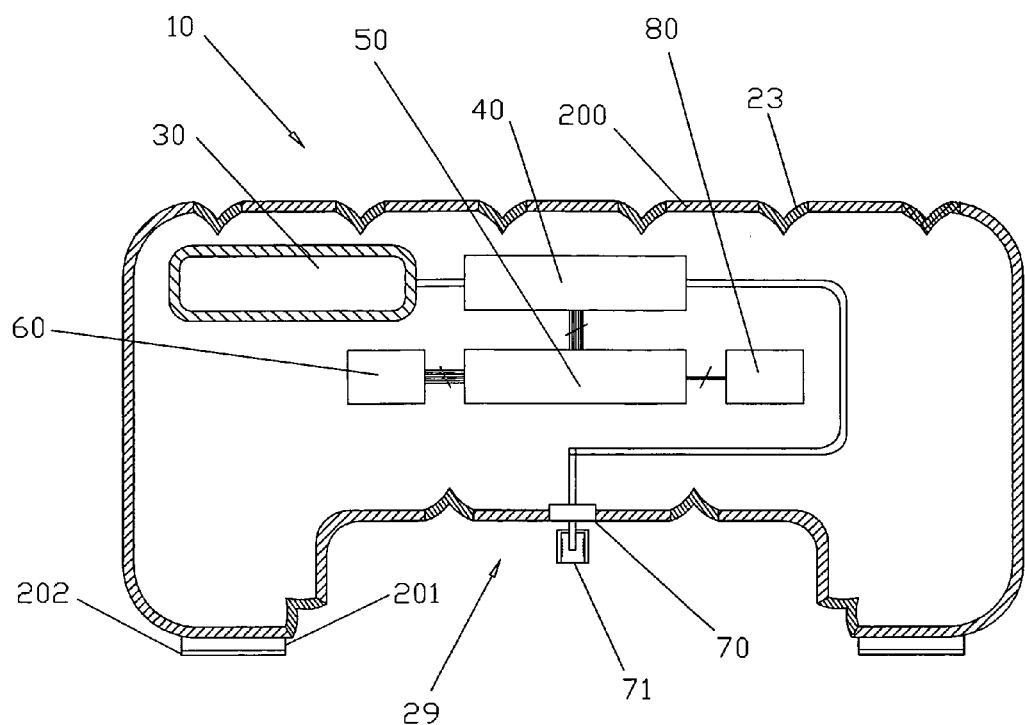
FIG. 9 is a sectional side view of an eighth exemplary embodiment of a fluid delivery device in accordance with the present invention.

FIG. 9 shows another exemplary embodiment of the fluid delivery device 10 which includes a housing 200 having flexible hinged sections 23 that allow the fluid delivery device 10 to flex during patient movement to prevent detachment and aid in patient comfort. The hinged sections 23 run along the length of the housing 20 and allow the fluid delivery device 10 to have flex along each axis of the hinged sections 23. Directions of the axes of the hinged sections 23 can be varied to provide optimum flexibility for various patient contours and areas of placement.

Figure 9A:
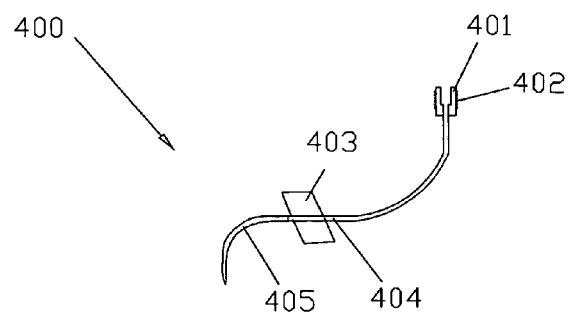
FIG. 9a is a perspective view of an infusion set compatible with an outlet assembly of the device of FIG. 9.

FIG. 9a shows a standard transcutaneous infusion set 400 consisting of a penetrating cannula 405, usually consisting of a needle bent to ninety degrees, a flexible tubing 404 and a Luer connector 401, which includes standard threads 402. The infusion set 400 may also include means for attaching to the skin of a patient, such as infusion set wings 403, which may have adhesive pads on their bottom side, or may be simply taped to the skin. This connection to the skin may not be necessary when used with fluid delivery device 10 with recessed housing 200. Infusion set 400 can be attached to fluid delivery device 10 by connecting the infusion set Luer connector 401 to the Luer connector 71 of the exit port assembly 70 of the device 10.

Figure 10:
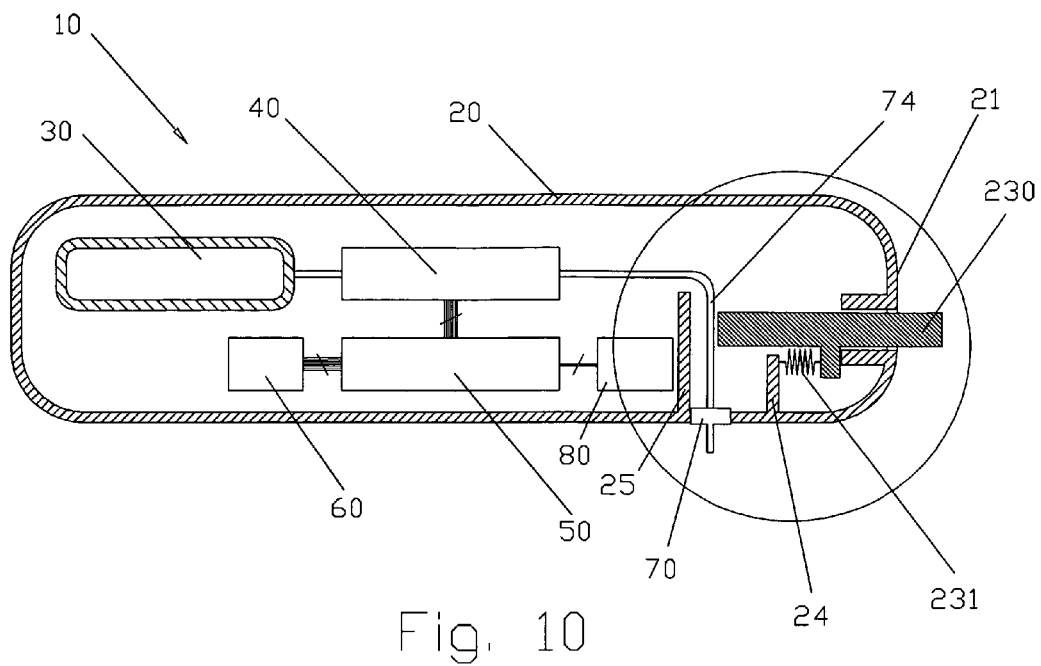
FIG. 10 is a sectional side view of a ninth exemplary embodiment of a fluid delivery device in accordance with the present invention, with a mechanical stop button of the device shown in the open position.
Figure 10A:
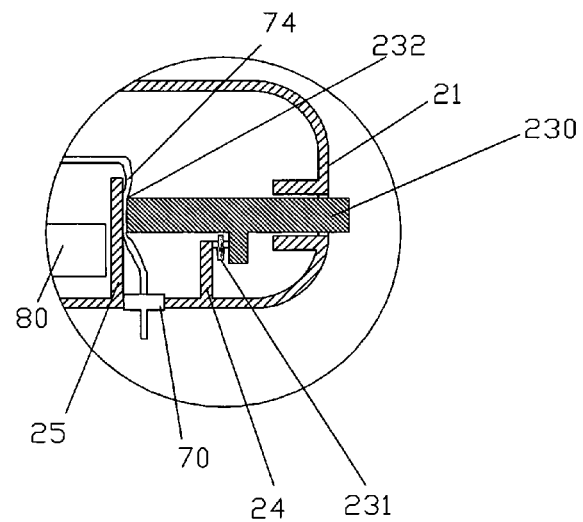
FIG. 10a is an enlarged sectional view of the stop button assembly of the device of FIG. 10 with the button shown in the closed position.

FIG. 10 shows another exemplary embodiment of the fluid delivery device 10 including a means for stopping flow without requiring use of the remote control device 100. In this embodiment, the means comprises a "t-shaped" stop button 230 that protrudes through the housing 20 and is maintained in a deactivated position through the force of stop button spring 231 The spring 231 is positioned between the stop button 230 and a portion 24 of the housing 20. Under normal conditions, fluid exits the dispenser 40, travels through the exit port tubing lumen 74 and exits the exit port assembly 70 unencumbered by stop button 230. As is shown in FIG. 10a, when stop button 230 is pressed such that it overcomes the force of the stop button spring 231, the stop button 232 compresses the exit port tubing lumen 74 against a second portion 25 of the housing 20, until the exit port tubing lumen 74 is fully occluded. In the embodiment shown, the stop button 230 protrudes through the housing 20. Alternatively, the device can be constructed such that, in the deactivated position, the stop button 230 is flush with the housing outer surface 21 to prevent undesired occlusion of flow by inadvertent pressing of the stop button 230. The button size and shape can be designed to accommodate an index finger, or the point of a pen. In addition, additional features can be added to have the button 230 latch and hold after being pressed against the lumen 74. The latching feature can be reversible, or can required removal and disposable of the fluid delivery device 10.

Figure 11:
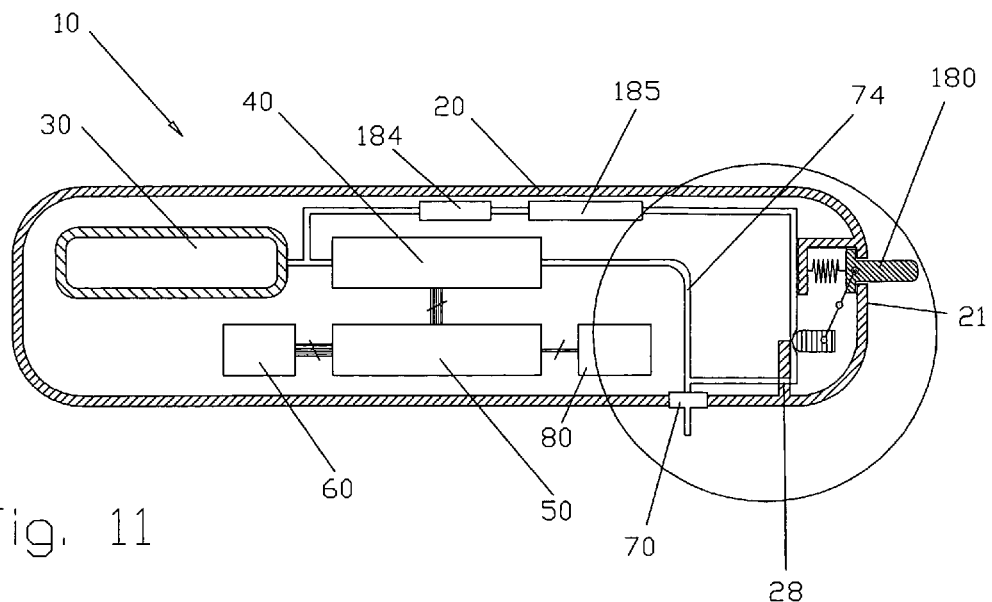
FIG. 11 is a sectional side view of a tenth exemplary embodiment of a fluid delivery device in accordance with the present invention.

FIG. 11 shows another exemplary embodiment of the fluid delivery device 10 including a means for delivering a fixed amount of fluid without requiring use of the remote control device 100. In certain circumstances, it may be desirable to administer a specific volume or bolus of fluid on demand without the use of the remote control device 100. Described here is an embodiment 10 wherein the user can press a mechanical bolus button 180 to release the bolus of the intended medicine.

Figure 11A:
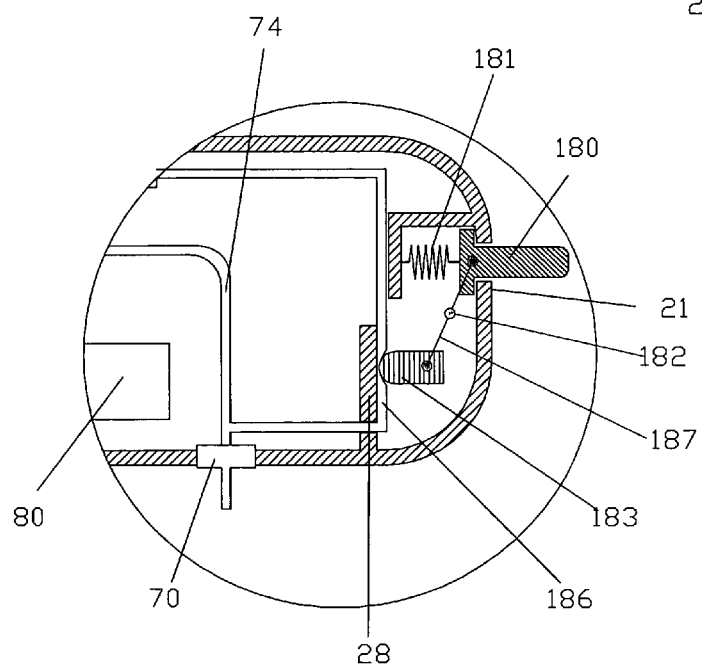
FIG. 11a is an enlarged sectional view of a bolus button assembly of the device of FIG. 11.

As also shown in FIG. 11a, the bolus button 180 is t-shaped and protrudes through the housing 20. The button 180 is maintained in a deactivated position through the force of bolus button spring 181 positioned between the bolus button 180 and an internal portion of the housing 20. The bolus button 180 is attached to a bolus release finger 183 via a pivoting bolus lever 187. The bolus lever 187 has a pivot 182 attached to the housing 20, and moves the bolus release finger 183 away from a bolus delivery tubing lumen 186 and a bolus button stop 28 of the housing when the bolus button 180 is depressed against the spring 181. The bolus delivery tubing 186 is in fluid communication with the exit port tubing lumen 74 and, thus, the exit port assembly 70. When bolus button 180 is not pressed, the bias from bolus button spring 181 causes the bolus release finger 183 to press against bolus delivery tubing lumen 186 which presses against the bolus button stop 28 to occlude the bolus delivery tubing lumen 186.

In order to deliver a fixed amount of fluid when the bolus button 180 is pressed, a bolus flow restrictor 184 and a bolus volume accumulator 185 are provided in the bolus delivery tubing 186. The bolus flow restrictor 184 acts as a flow limiter to prevent free flow of fluid from the reservoir 30, and creates a minimum lock-out period between full bolus volumes. Assuming in this particular embodiment that the reservoir 30 is maintained at a pressure above atmospheric pressure, the flow rate of the flow restrictor 184 is chosen to be much slower than the rate at which the bolus volume should be delivered.

The bolus volume accumulator 185 expands with the inflow of fluid from the flow restrictor 184 as long as the bolus release finger 183 is occluding the bolus delivery tubing 186. The amount of expansion of the bolus volume accumulator 185 equals the bolus volume to be delivered. When the bolus button 180 is depressed, the bolus volume of fluid maintained in the bolus volume accumulator 185 is dispensed through the bolus delivery tubing lumen 186 and out of the exit port assembly 70.

The time to dispense the bolus dose should be short since there are no downstream flow restrictors, and the user could be instructed to hold the button down for a required time, not more than a few seconds. Alternative designs could latch the bolus button 180 for a specific amount of time only, as the button must be released to prevent continued flow via the flow restrictor 184. After the bolus button 180 is pressed, bolus volume accumulator 185 fluid is delivered until the pressure in bolus volume accumulator 185 reaches atmospheric pressure. Release of bolus button 180 causes the bolus lever 187 to rotate back, pivoting around bolus pivot 182 until bolus release finger 183 is occluding bolus delivery tubing lumen 186 by pressing it against housing button stop 28. Bolus volume accumulator 185 again expands an amount equal to the next bolus volume to be delivered as fluid from reservoir 30 passes through bolus flow restrictor 184 until the pressure in bolus volume accumulator 185 equals the pressure in reservoir 30.

In FIGS. 11 and 11a, the bolus button 180 is shown protruding through housing 20. Alternatively, in the deactivated position, bolus button 180 may be flush with the housing outer surface 21 to prevent undesired bolus delivery by inadvertent pressing of bolus button 180. In addition, while the figure shows a design that allows multiple depressions of the bolus button 180, alternative designs can make the bolus button 180 activation a one-time event, requiring the user to replace the fluid delivery device 10 or locate the remote control device 100.

Figure 12:
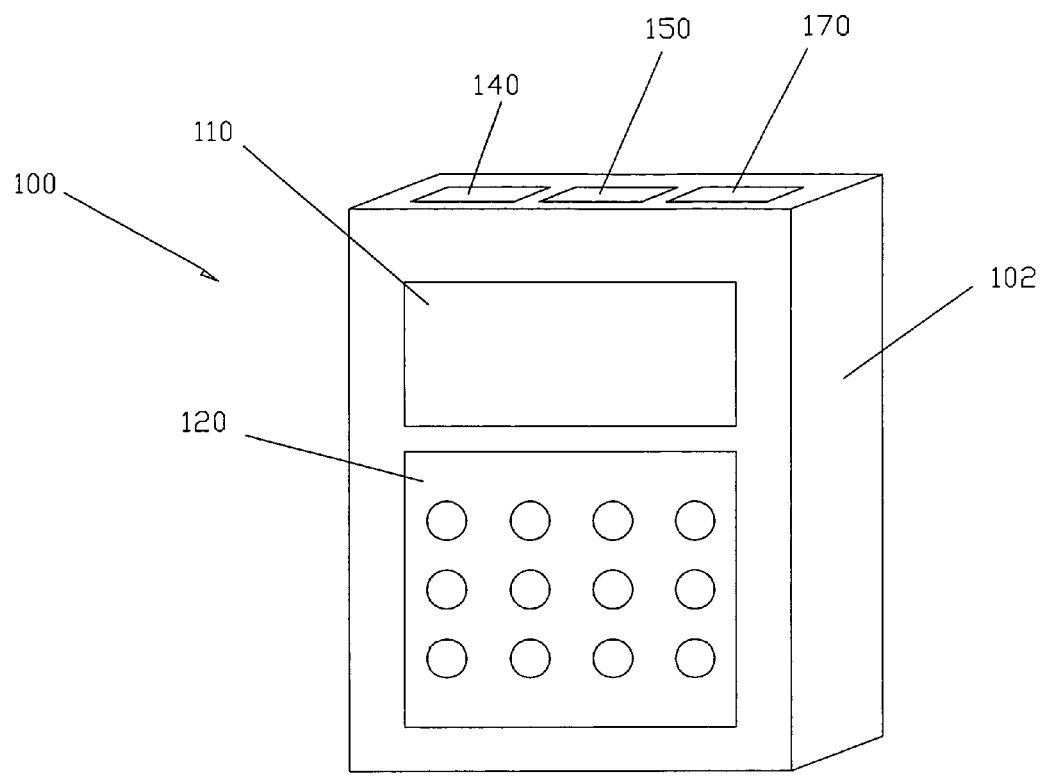
FIG. 12 is a perspective view of another exemplary embodiment of a remote control device in accordance with the present invention.
Figure 12A:
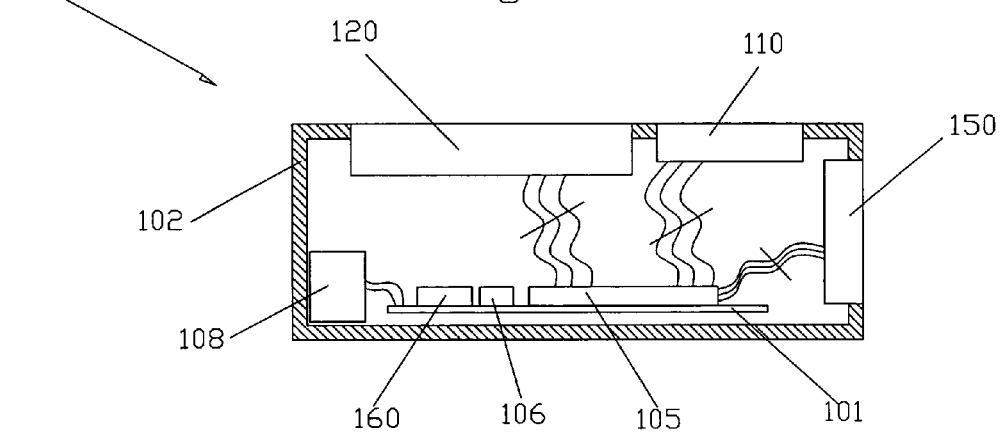
FIG. 12a is a sectional side view of the remote control device of FIG. 12.

FIGS. 12 and 12a depict a exemplary embodiment of the remote control device 100 of the present invention. The remote control device 100 is a hand held device that includes a controller housing 102, on which is mounted a visual display 110, such as a liquid crystal display or LCD. The visual display 110 can visually indicate status of programming, amounts, timing, and other parameters of medicinal fluid delivery. Other information can include time of day, address book, to do lists, and calendar information and potentially an entertainment interface such as a computer game. Another use of the visual display 110 is to display information received or to be sent to devices other than the fluid delivery device 100, such as a glucometer used by diabetic patients or other diagnostic device, especially those whose information is related to the desired infusion rates and volumes to be delivered by fluid delivery device 10. The remote control device 100 may have a diagnostic device, such as a blood glucose monitor or glucometer, or an implantable glucose sensor reader, integrated into it, simplifying the requirements of the patient by not having to carry and maintain two separate devices. Other diagnostic devices include but are not limited to blood diagnostic devices, electrocardiography devices and readers, electroencephalogram or EEG devices and readers, blood pressure monitors and pulse oxymetry devices. Alternative to full integration of the diagnostic device, would be connection to the device via wireless or hardwired communication means, to perform a transfer of information.

The visual display 110 can also include information such as warning and alarm conditions based on the status of the fluid delivery device 100. Elements such as indicator lights, buzzers, and vibrational alarms may also be included in the remote control device 100 as alternative or redundant means for communicating information to the user.

The user can get information and adjust the programming of the device by depressing various electromechanical switches also mounted on controller housing 102. These switches may be joined in a bank of switches and included in membrane keypad 120 as shown in FIGS. 11 and 11*a* and as is common with hand held electronic devices. It is preferred that the choice of electromechanical switches of the membrane keypad 120 interface with the visual display 110 in a menu driven fashion making reading information and programming the device more user friendly for the user. In an alternative embodiment, the visual display 110 and membrane keypad 120 can be combined into a single device such as a touch screen display, also common to electronic devices. Combination of touch screen displays, membrane keypads and singular switches may all be integrated into the remote control device 100.

The remote control device 100 may include various electromechanical jacks, which can accept electromechanical plugs from various devices. Shown in the figure are three plugs, a bar code reader 140, a glucometer port 150 and a computer port 170. These ports can allow two way transfer of information to enhance the capabilities of remote control device 100 and improve its user friendliness. FIG. 12*a* shows a schematic cross section of the remote control device 100. The membrane keypad 120 and visual display 110 are attached to the controller electronics 105. Depicted is glucometer port 150 attached to the controller electronics 105. Bar code reader 140 and computer port 170 are also attached to the controller electronics, not shown. The controller electronics are mounted and soldered to the controller printed circuit board 101 as is the controller communication element 160.

The controller communication element 160 is designed to transmit signals, or information to the communication element 60 of the fluid delivery device 10. The controller electronics 105 act as a "translator" in translating user inputs received through the user interfaces 120 into signals for transmission by the controller communication element 160. In a preferred embodiment, both the communication element 60 and the controller communication element 160 are two way communication assemblies allowing two way communication between the remote control device 100 and fluid delivery device 10. In order to send wireless information the communication element 60 and the controller communication element 160 may include inductive wire loops or other transmitting antenna means. Information can be sent using amplitude or frequency modulation, and can be broadcast in the radio frequency, or RF range. Standard information confirmation techniques such as handshaking or checksum protocols can be used to insure accurate information transfer. With two-way communication, when errors are detected, the transfer can be repeated until acceptable, a similar technique to that utilized with two way pager technology commonplace today.

If the fluid delivery device 10 is prefilled prior to patient use, the electronic memory of local processor 50 may contain information regarding the fluid including but not limited to type or name, concentration, amount, volume, additional drugs in solution and any diluting agents. This information can be transmitted from the fluid delivery device 10 via its communication element 60, and uploaded into the remote control device 100 via its controller communication element 160. Other information may be factory installed into the fluid delivery device 10 including but not limited to manufacturing date, expiration date, sterilization date, therapy information such as defined flow profiles and even patient or hospital information. This information can be uploaded into the remote control device 100 as described above, and the remote control device 100 may adjust its internal programming based on the information received.

In a preferred embodiment, the electronic memory of the fluid delivery device 10 includes the latest program of the remote control device 100 available at the time of manufacture of the fluid delivery device 10. Similarly, the electronic memory of the remote control device 100 includes the latest program of the fluid delivery device 10, available at the time of manufacture of the remote control device 100. At the first communication between the remote control device 100 and the fluid delivery device 10, a program check is performed, and if a newer software version for either device is available from the other device, and the existing hardware is compatible, another feature which can be programmed into both devices, the newer program is downloaded into memory and used by the upgraded device. The embedded program may be contained in read only memory, or ROM, while the downloaded program can be written into electronically writeable memory. The automatic update feature, available for each device to upgrade the other, is another way to make sure the user has the best available product for use.

Another advantageous feature associated with two way communication is the addition of a proximity alarm. The design of the fluid delivery device 10 and remote control device 100 electronics can be such that when the distance between the two devices is greater than a particular radial length, one or both of the devices will alert the user, potentially with an audio alarm. The alarming distance should be chosen so that it is less than the maximum communication range of the two devices. A method of creating the alarm is for the fluid delivery device 10 to send out frequent packets of information at a predetermined rate and at an amplitude or power less than the normal communication power, providing a safety margin for the proximity detection. The remote control device 100 is programmed to expect to receive this communication at the predetermined rate, and lack of receipt of one or more of these packets, causes the remote control device 100 to activate its audio alarm 106. Alternatively or additionally, a vibrational alarm may be included. Proximity alarms may be included that do not require two way communication, by integrating a device such as a magnet into the housing 20 of fluid delivery device 10, and integrating magnetic field detection means into the remote control device 100. When the magnetic field detection means of the remote control device 100 do not detect the presence of the magnetic field of the fluid delivery device 10, the remote control device 100 activates the controller audio alarm 106.

The remote control device 100 includes a controller power supply 108 that powers the various electronic components including the controller electronics 105, controller audio alarm 106. The controller power supply 108 may be a standard battery and in the preferred embodiment, the power supply 108 may be replaceable by the user by removing a battery door, not shown, and replacing after power supply 108 is inserted and attached. In an alternative embodiment, the power supply is integrated into the remote control device 100, and can be recharged with a separate device or contains enough power to supply the device for its intended length of use.

The fluid delivery device 10 of the present invention may be sold to hospitals, pharmacies, outpatient centers or the patients themselves. If the fluid delivery device is intended for short term or disposable use, it may be practical to sell each device with various accessories or groups of accessories that are convenient for the user. It may be desirable for certain parts of the fluid delivery device, or accessories such as an attachable transcutaneous infusion set, such as that described hereinabove, to be packaged sterilized in a protective packaging. Proper aseptic maintenance of the portion of the skin that receives the transcutaneous access is important to prevent infection. FIGS. 13, 13a, 13b and 13c depict various components that may be packaged together in kit form.

Figure 13:
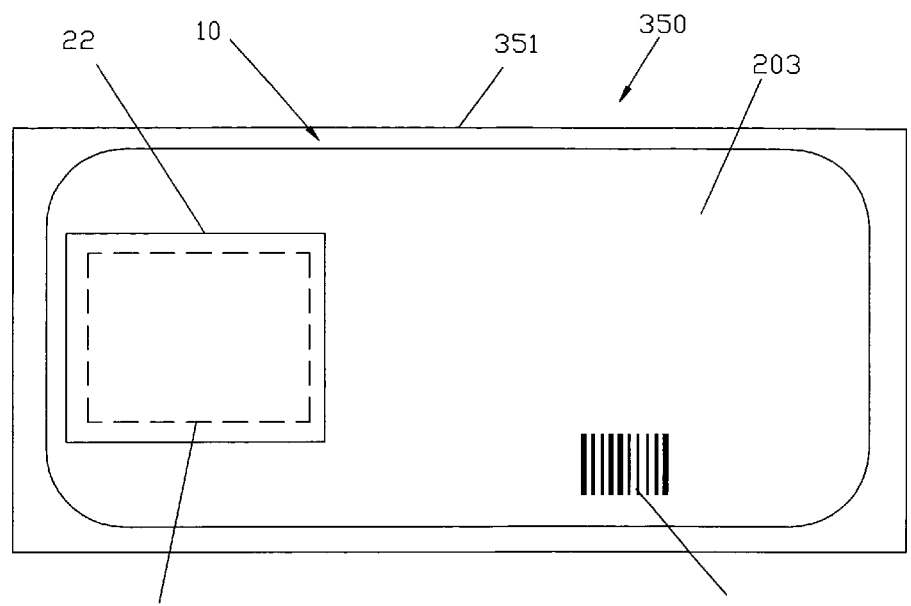
FIG. 13 is a top plan view of an eleventh exemplary embodiment of a fluid delivery device in accordance with the present invention.

FIG. 13 shows the fluid delivery device of the present invention including means for viewing the status of the reservoir 30 and an information barcode 26 with a sterilized device in a sterile assembly pack 350. The device may be packaged separately or with various other kit components. The fluid delivery device may be packaged sterile entirely in a device pouch 351, intended to allow sterilization and maintain sterility. Such pouches often are constructed of materials such as TYVEK, a product of Dupont. The sterile assembly pack 350 consists of the fluid delivery device 10 of the present invention, sealed in the device pouch 351 as is shown in FIG. 13. Alternatively, a portion of the fluid delivery device surrounding the exit port assembly 70 may be covered, sealed and sterilized with a sterility maintaining covering (not shown).

The top of the housing 20, or housing top side 203 includes a housing transparent window 22 located above the reservoir 30. The transparency of the housing transparent window 22 and design of the reservoir 30 are such that the patient can determine information regarding status of the reservoir 30 by viewing through the housing transparent window 22. Such information can include amount of drug remaining or presence of a leak. Alternatively, the entire housing 20 may be transparent yielding similar visual indications.

Also included in the fluid delivery device 10 of this embodiment is an information barcode 26 which can include various pieces of information regarding the status of that particular fluid delivery device 10 such as type, volume and concentration of drug prefilled in the device, expiration date of device or drug, manufacture date of device or drug, serial numbers, lot numbers, hospital name, clinician name, patient name, prescription requirements and various other pieces of information. The barcode information can be read into a hospital or home computer, or in the preferred embodiment is uploaded via a barcode reader integral to the remote control device 100. The fluid delivery device 10 and remote control device 100 electronics and programming can be designed such that the bar code must be read prior to programming or otherwise using the fluid delivery device 10. This feature can greatly reduce programming errors such as those associated with the patient entering drug information. If the patient were to enter a drug concentration that was incorrect, and did all the remaining programming in units of drug, instead of volume, which is common practice, while the device would function properly, all of the volumes delivered would be inaccurate based on the ratio of the incorrect concentration entered versus the true concentration of the drug being delivered. Many drugs are available in multiple concentrations such as insulin often made available to patients in 40, 50 and 100 units per ml concentrations.

Figure 13A:
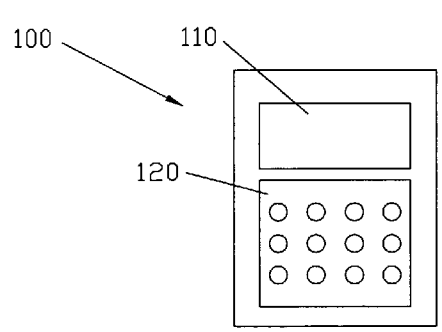
FIG. 13a is a top plan view of a remote controller to be combined with the fluid delivery device of FIG. 13 as part of a kit in accordance with the present invention.

FIG. 13a shows the remote control device 100 of the present invention that could be packaged or provided as a kit with one or more of sterile package assembly 350, including at least one fluid delivery device 10. There is no need for the remote control device 100 to be sterilized, so if the fluid delivery device 10 was sterilized, one or more sterile package assembly 350 can be boxed or otherwise packaged with a single remote control device 100 along with one or more other devices 10.

Figure 13B:
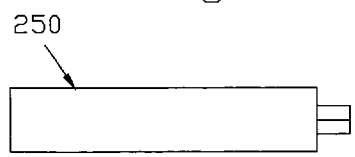
FIG. 13b is a top plan view of an insulin cartridge to be combined with the fluid delivery device of FIG. 13 as part of a kit in accordance with the present invention.

FIG. 13b shows a therapeutic fluid supply 250, which may consist of a vial of drug such as insulin. The drug, in one or more vials, which has been sterilized and made otherwise biocompatible for use, can be packaged with one or more sterile package assemblies 350 as well as with one or more remote control devices 100. Additional devices may be included in the kit if desired.

Figure 13C:
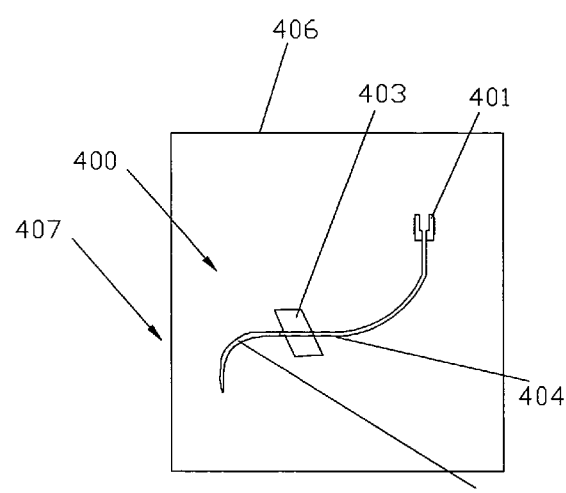
FIG. 13c is a top plan view of a sterile infusion set to be combined with the fluid delivery device of FIG. 13 as part of a kit in accordance with the present invention.

FIG. 13c shows a sterile infusion set assembly 407 including the transcutaneous infusion set 400 described hereinabove packaged in an infusion set pouch 406. The infusion set 400 includes an infusion set Luer 401 connected to infusion set flexible tubing 404 and terminating in an infusion set penetrating cannula 405. An optional set of infusion set wings 403 can be included to attach the infusion set 400 to the patient's skin. In the preferred embodiment of fluid delivery device 100, the transcutaneous delivery means are integrated into exit port assembly 70, however in an alternative embodiment, the exit port assembly 70 can be attached to infusion set 400. In this particular embodiment, it may be desirable to kit sterile infusion set assemblies 407 with any quantity of one or more of the sterile assembly packs 350, the fluid delivery device 10, the remote control device 100 or the therapeutic fluid supply 250.

The fluid delivery device 10 of the present invention is intended to be low cost and potentially disposable. It may be advantageous for one or more of the components to be biodegradable, since replacement of the device every two to five days has many advantages, it would also generate a fair amount of waste. The fluid delivery device 10 may include a preinstalled battery as its power supply 80. In order to prevent the battery from powering the electronics of fluid delivery device 10 before its intended use, a mechanical switch may be included, connecting the battery contacts to the electronics prior to programming with the remote control device 100. A simplistic version of the switch design may be an insulating material between the battery contacts of power supply 80 and the electrical connection to the local processor 50. The insulating material could be designed to protrude through housing 20, and be removable by the user, not shown. The user could pull the insulating material and remove it, simultaneously connecting the battery contacts with the electrical connection to the local processor.

The fluid delivery device 10 of the present invention may be filled with the therapeutic fluid by the device manufacture, a pharmaceutical company, or another manufacturer prior to its shipment to the hospital, pharmacy or patient. Certain drugs require refrigeration or other special environmental conditions, requiring the prefilled fluid delivery device to be refrigerated or otherwise handled to meet special requirements. Insulin is a drug that requires refrigeration if it is to be stored for a prolonged period of time. Hoechst, of Frankfurt Germany, is developing insulin that is stable at higher temperatures. Drugs that are stable at room temperature, such as the developmental insulin of Hoechst, allow simple filling and handling of the fluid delivery device 10, greatly simplifying the requirements for the patient.

Various methods of using the fluid delivery device 10 are included in the present invention and described above. The method of programming the fluid delivery device 10 with remote programmer 100 as well as the attachment and use of the peripheral devices including transcutaneous infusion sets and diagnostic devices such as glucometers are described. Also relevant is the ability to update the internal programming of either the fluid delivery device 10 or the remote control device 100 by the corresponding device. Methods of filling the fluid delivery device 10 with therapeutic fluid during the manufacturing process as well as by the user have been described. Methods and timing of sterilization and packaging of part or all of the fluid delivery device 10 and therapeutic fluid have also been described.

Although exemplary embodiments of the invention have been shown and described, many changes, modifications and substitutions may be made by those having ordinary skill in the art without necessarily departing from the spirit and scope of this invention. For example, the fluid delivery device of this invention is intended to be low cost, light weight, simple to use and potentially disposable by removing a majority of the user interface, including electromechanical switches, from the fluid delivery device, and including a separate controller to replace those functions. A reservoir, fluid dispenser, transcutaneous fluid administration means, solid state electronics and wireless communications are included in the fluid delivery device to perform its intended function. While various means for reservoir construction, pressurization means, fluid pumping means, fluid metering means, transcutaneous delivery, electronic control and wireless communications have been discussed in this application, alternatives to each of these areas can be made without departing from the spirit of the invention.

In addition, where this patent application has listed the steps of a method or procedure in a specific order, it may be possible (or even expedient in certain circumstances) to change the order in which some steps are performed, and it is intended that the particular steps of the method or procedure claims set forth hereinbelow not be construed as being order-specific unless such order specificity is expressly stated in the claim.

What is claimed is:

1. A remote control device for successively providing flow instructions to at least two disposable fluid delivery devices, comprising:

user input components for receiving user inputs regarding flow instructions for the fluid delivery devices;

a wireless transmitter for transmitting the flow instructions for the fluid delivery devices; and a remote processor connected to the user input components and the wireless transmitter and programmed to assemble the flow instructions for the fluid delivery devices based upon the user inputs received through the user input components, and transmit the flow instructions successively to the fluid delivery devices through the wireless transmitter;

wherein the remote processor includes a computer program comprising a set of instructions and wherein said set of instructions can be modified by the fluid delivery devices.

2. A system for delivering fluid transcutaneously to a patient including the remote control device of claim 1 and further comprising at least two fluid delivery devices void of user input components.

3. The remote control device of claim 1, wherein the user input components include a membrane keypad.

4. The remote control device of claim 1, wherein the user input components include a touch screen display.

5. The remote control device of claim 1, wherein the remote processor includes programming for updating one or more computer programs of the fluid delivery devices.

6. The remote control device of claim 1, wherein the flow instructions for the fluid delivery devices include a variable rate infusion of fluid.

7. The remote control device of claim 1, wherein the remote processor is further programmed to transmit the flow instructions simultaneously to the fluid delivery devices through the wireless transmitter.

8. The remote control device of claim 1, wherein the wireless transmitter utilizes radio frequency signals.

9. The remote control device of claim 1, further comprising a wireless receiver for receiving flow information from the fluid delivery devices, and wherein the remote processor is connected to the wireless receiver and further programmed to receive the flow information from the fluid delivery devices through the wireless receiver.

10. The remote control device of claim 9, wherein the remote processor is programmed to receive the flow information successively from the fluid delivery devices through the wireless receiver.

11. The remote control device of claim 9, wherein the remote processor is programmed to receive the flow information simultaneously from the fluid delivery devices through the wireless receiver.

12. The remote control device of claim 1, further comprising an input port for connecting with a physiologic sensor separate from the remote control device, and wherein the remote processor is connected to the input port and programmed to receive physiologic information from the physiologic sensor through the input port.

13. The remote control device of claim 12, wherein the physiologic information is blood glucose information.

14. The remote control device of claim 1, further comprising a blood glucose sensor adapted to receive a tool containing a blood sample and provide a blood glucose measurement, and wherein the remote processor is connected to the blood glucose sensor and programmed to receive the blood glucose measurement.

15. The remote control device of claim 1, wherein the remote processor further comprises programming to perform a user function unrelated to the flow instructions.

16. The remote control device of claim 15, wherein the user function is a non-medical function.

17. The remote control device of claim 16, wherein the user function comprises at least one of an electronic calendar, an electronic address book, an electronic to do list, an email function, an internet access function, a wireless telephone function, and an electronic game function.

18. A remote control device for successively receiving flow information from at least two disposable fluid delivery devices, comprising:
  user output components for providing user outputs regarding flow information from the fluid delivery devices;
  a wireless receiver for receiving the flow information from the fluid delivery devices; and
  a remote processor connected to the user output components and the wireless receiver and programmed to successively receive the flow information from the fluid delivery devices through the wireless receiver and convert the flow information to user outputs and provide the user outputs to the user output components;
  wherein the remote processor includes a computer program comprising a set of instructions and wherein said set of instructions can be modified by the fluid delivery devices.

19. A system for delivering fluid transcutaneously to a patient including the remote control device of claim 18 and further comprising at least two fluid delivery devices void of user output components.

20. The remote control device of claim 18, wherein the user output components include at least one of a liquid crystal display, a light emitting diode, a vibrational transducer and an audio transducer.

21. The remote control device of claim 18, wherein the user output components include a touch screen display.

22. The remote control device of claim 18, wherein the remote processor includes programming that can modify the set of instructions that comprise one or more programs of the fluid delivery devices.

23. The remote control device of claim 18, wherein the flow information includes variable rate infusion of fluid information.

24. The remote control device of claim 18, wherein the remote processor is further programmed to receive the flow information simultaneously from the fluid delivery devices through the wireless receiver.

25. The remote control device of claim 18, wherein the wireless receiver utilizes radio frequency signals.

26. The remote control device of claim 18, further comprising a wireless transmitter for transmitting flow instructions to the fluid delivery devices, and wherein the remote processor is connected to the wireless transmitter and further programmed to transmit the flow instructions to the fluid delivery devices through the wireless transmitter.

27. The remote control device of claim 26, wherein the remote processor is programmed to transmit the flow instructions successively to the fluid delivery devices through the wireless transmitter.

28. The remote control device of claim 26, wherein the remote processor is programmed to transmit the flow instructions simultaneously to the fluid delivery devices through the wireless transmitter.

29. The remote control device of claim 18, further comprising an input port for connecting with a physiologic sensor separate from the remote control device, and wherein the remote processor is connected to the input port and programmed to receive physiologic information from the physiologic sensor through the input port.

30. The remote control device of claim 29, wherein the physiologic information is blood glucose information.

31. The remote control device of claim 18, further comprising a blood glucose sensor adapted to receive a tool containing a blood sample and provide a blood glucose measurement, and wherein the remote processor is connected to the blood glucose sensor and programmed to receive the blood glucose measurement.

32. The remote control device of claim 18, wherein the remote processor further comprises programming to perform a user function unrelated to the flow information.

33. The remote control device of claim 32, wherein the user function is a non-medical function.

34. The remote control device of claim 33, wherein the user function comprises at least one of an electronic calendar, an electronic address book, an electronic to do list, an email function, an internet access function, a wireless telephone function, and an electronic game function.

35. A remote control device for successively providing flow instructions to, and receiving flow information from, at least two disposable fluid delivery devices, comprising:
  user input components for receiving user inputs regarding flow instructions for the fluid delivery devices;
  user output components for providing user outputs regarding flow information from the fluid delivery devices;
  a wireless transmitter for transmitting the flow instructions for the fluid delivery devices;
  a wireless receiver for receiving the flow information from the fluid delivery devices; and
  a remote processor connected to the user input components, the user output components, the wireless transmitter, and the wireless receiver, and programmed to successively communicate with the fluid delivery devices and,
    assemble the flow instructions for each of the fluid delivery devices based upon the user inputs received through the user input components, and transmit the flow instructions to the fluid delivery device through the wireless transmitter, and
    receive the flow information from each of the fluid delivery devices through the wireless receiver and convert the flow information to user outputs and provide the user outputs to the user output components;
  wherein the remote processor includes a computer program comprising a set of instructions and wherein said set of instructions can be modified by the fluid delivery devices.

36. A system for delivering fluid transcutaneously to a patient including the remote control device of claim 35 and further comprising at least two fluid delivery devices void of user input components and void of user output components.

37. The remote control device of claim 35, wherein the user input components include a membrane keypad.

38. The remote control device of claim 35, wherein the user input components include a touch screen display.

39. The remote control device of claim 35, wherein the remote processor includes programming for updating one or more computer programs of the fluid delivery devices.

40. The remote control device of claim 35, wherein the flow instructions for the fluid delivery devices include a variable rate infusion of fluid.

41. The remote control device of claim 35, wherein the wireless transmitter utilizes radio frequency signals.

42. The remote control device of claim 35, further comprising an input port for connecting with a physiologic sensor separate from the remote control device, and wherein the remote processor is connected to the input port and programmed to receive physiologic information from the physiologic sensor through the input port.

43. The remote control device of claim 42, wherein the physiologic information is blood glucose information.

44. The remote control device of claim 35, further comprising a blood glucose sensor adapted to receive a tool containing a blood sample and provide a blood glucose measurement, and wherein the remote processor is connected to the blood glucose sensor and programmed to receive the blood glucose measurement.

45. The remote control device of claim 35, wherein the remote processor further comprises programming to perform a user function unrelated to the flow instructions.

46. The remote control device of claim 45, wherein the user function is a non-medical function.

47. The remote control device of claim 46, wherein the user function comprises at least one of an electronic calendar, an electronic address book, an electronic to do list, an email function, an internet access function, a wireless telephone function, and an electronic game function.

48. The remote control device of claim 35, wherein the user output components include at least one of a liquid crystal display, a light emitting diode, a vibrational transducer and an audio transducer.

49. The remote control device of claim 35, wherein the user output components include a touch screen display.

50. The remote control device of claim 35, wherein the flow information includes variable rate infusion of fluid information.

51. The remote control device of claim 35, wherein the wireless receiver utilizes radio frequency signals.

52. The remote control device of claim 35, wherein the remote control device is further programmed to confirm communication with the fluid delivery device.

53. The remote control device of claim 18, wherein the remote control device is further programmed to confirm communication with the fluid delivery device.

54. The remote control device of claim 1, wherein the remote control device is further programmed to confirm communication with the fluid delivery device.

* * * * *